(12) United States Patent
Sleep

(10) Patent No.: US 6,379,924 B1
(45) Date of Patent: Apr. 30, 2002

(54) PROTEIN EXPRESSION STRAINS

(75) Inventor: Darrell Sleep, West Bridgford (GB)

(73) Assignee: Delta Biotechnology Ltd., Nottingham (GB)

( * ) Notice: Subject to any disclaimer, the term of this patent is extended or adjusted under 35 U.S.C. 154(b) by 0 days.

(21) Appl. No.: 09/446,047

(22) PCT Filed: Jun. 26, 1998

(86) PCT No.: PCT/GB98/01885

§ 371 Date: Dec. 15, 1999

§ 102(e) Date: Dec. 15, 1999

(87) PCT Pub. No.: WO99/00504

PCT Pub. Date: Jan. 7, 1999

(30) Foreign Application Priority Data

Jun. 26, 1997 (GB) .............................................. 9713412

(51) Int. Cl.$^7$ ................................................ C12P 21/02
(52) U.S. Cl. ...................... 435/69.1; 435/483; 435/484; 435/254.11; 435/254.2; 435/254.21
(58) Field of Search ................................ 435/69.1, 483, 435/484, 254.11, 254.2, 254.21; 530/350

(56) References Cited

U.S. PATENT DOCUMENTS 4,777,242 A * 10/1988 Nelles ......................... 530/351
4,935,350 A    6/1990 Patel et al.

FOREIGN PATENT DOCUMENTS

WO    WO97/12045    4/1997

OTHER PUBLICATIONS

Betting & Seufert (1996) *J. Biol. Chem.* 271, 25790–25796.
Sleep et al (1991) *Bio/Technology* 9, 183–187.
Seufert & Jentsch (1990) *The EMBO J.* 9, 543–550.
Cook et al (1993) *Biochemistry* 32, 13809–13817.
Wilkinson (1990) *Meth. Enzymol.* 185, 387–397.
Treier et al (1992) *The EMBO J.* 11, 367–372.
Matuschewski et al (1996) *J. Biol. Chem.* 271, 2789–2794.
Jensen et al (1995) *J. Biol. Chem.* 270, 30408–30414.
Zhen et al (1993) *Mol. Cell. Biol.* 13, 1371–1377.
Jentsch (1992) *Ann. Rev. Genet.* 26, 179–207.
Rose & Broach (1990) *Methods Enzymol.* 185, 234–279.
Boeke et al (1987) *Methods Enzymol.* 154, 164–175.
Compagno et al (1993) *Biotechnol. Prog.* 9, 594–599.
Compagno et al (1996) *Yeast* 12, 199–205.
Apostol & Greer (1988) *Gene* 67, 59–68.

* cited by examiner

Primary Examiner—James Ketter
(74) Attorney, Agent, or Firm—Naomi S. Biswas

(57) ABSTRACT

The use of a means to vary Ubc4p or Ubc5p activity in a fungal cell to control the copy number of a plasmid in the cell. The level of Ubc4p or Ubc5p activity may be reduced/abolished (for example by gene deletion, mutagenesis to provide a less active protein, production of antisense mRNA or production of competitive peptides) to raise the copy number and increase yield of a protein encoded by the plasmid.

38 Claims, 22 Drawing Sheets

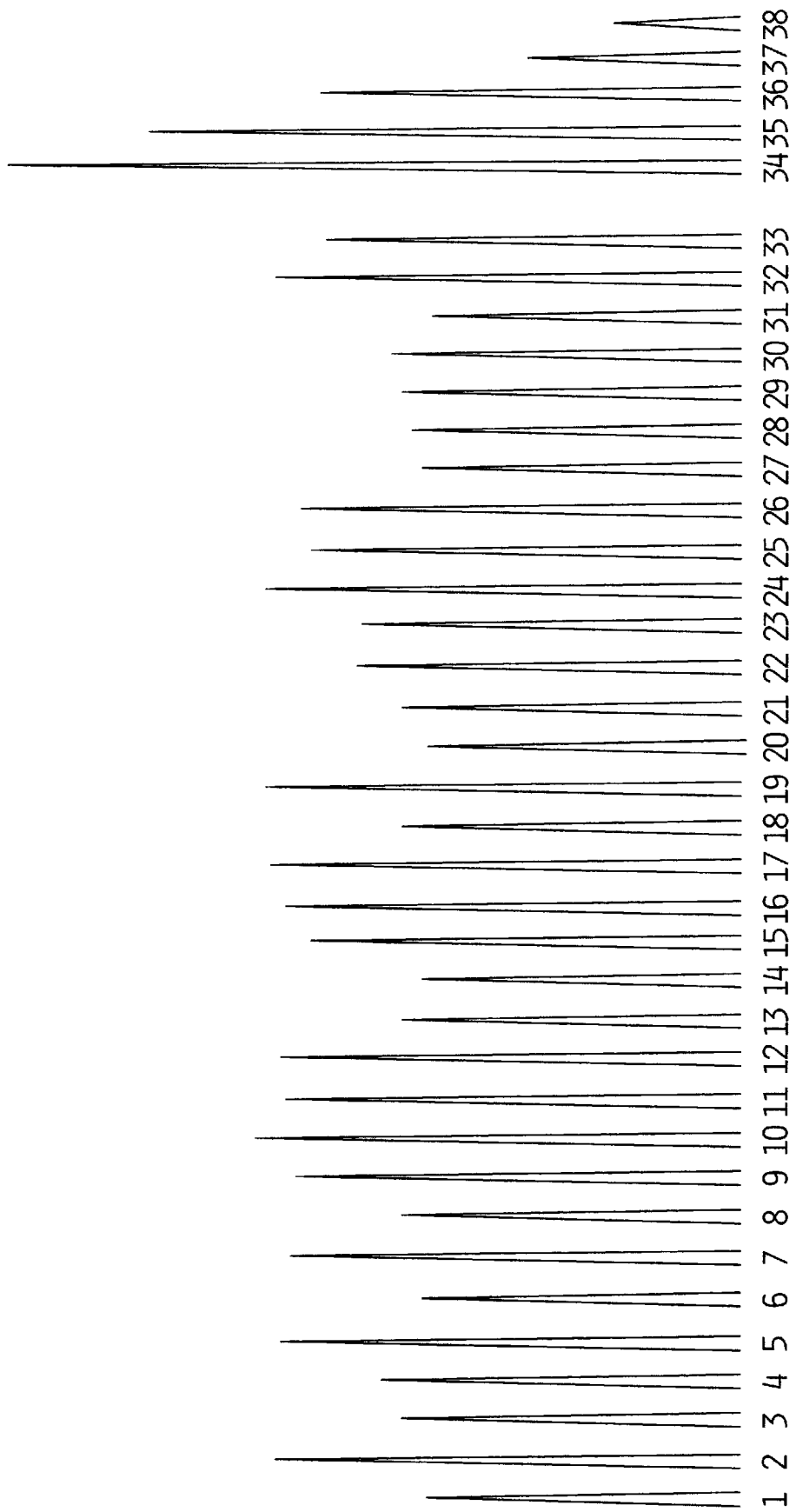
FIG_2

FIG_3

CTGCAGTACTCTTTTGATTCTGTAGGAAACCAGCGAAGAACGTACTCTTGCCTGA
PstI

AGAGAAGTTTTTTTTATTTATTTATATTTTGTTCTGGAAGCTCTTTACAGAATGGA

GTAGGAAAATATATAGAGAGGAAAAGCGAAATCGTTACGAGAATAAATAATCAA

GAAAAGAAACTTGAACTTGGCTTTTCCAAAACAACAGAAGTAGCGTTAATTTACT

TTCACCGTAAAATTCAACTCTTTAAATATAGTCCACTTAGTAAATTCTTGCCAATT

TGCATGATAAATTCGAACCCATTCCTCAAAATAAAGGGTCCTCATACATTCCATG

GAAAGAAAGTTTTCTTGAACATTAAGAATAAAAAGGCAAAAAAGAAAAAAAAAA

GCACAGCTACTGTTTTAGTCAACATTCCTTTCTCACTGGAATGCACAAGGTGTCAT

TCCTGAACAAGGGTAACTGCACTATTCATATGTCCACCTTATGACTTCATAAAAA

GTTTGACAATAAGTAGTCTTACGTGATAAGAAATGATGTAACATAAGGCTAATGT

CCTTATTCCAAAGTATCTCATTTATACAATAAACAAAACTGATCTTACCGCCTATC

CTCCTCTCCGCACTAATCAATTGTTATAGTTTTTCTCGAAGCGAGGATCAAATGGC

CGAGCAACAGGAAAAGGAGTACCGGCGGTCACATGGTCTGCGAGATTTTTCCCGC

TGCGGAAAAACCTGGCAACAGCTCACCTTGAAAGGCCTTGGCCTGTATTTTTCTTT

FIG. 3A

TTTCTTCATCCTTCTTTCTTTTTCTTTATTCTTATTTTTCATCTTAATAAATAATCCA

GAGAATAAATCTATCCTGAAAAAAAATAAAGTAAAGAAGCCAGGAAAATCACTA

TCGCCACAAGTAAATAAATTTCACTGACTATAGAGTACATACATAAACAAGCATC

CAAAAAAACATGTCTTCTTCTAAACGTATTGCTAAAGAACTAAGTGATCTAGAAA

|ORF START

GGTATGTCTAAAGTTATGGCCACGTTTCAAATGCGTGCTTTTTTTTTAAAACTTAT

———————————— INTRON ————————————

GCTCTTATTTACTAACAAAATCAACATGCTATTGAACTAGAGATCCACCTACTTCA

TGTTCAGCCGGTCCAGTCGGCGATGATCTATATCACTGGCAAGCATCCATCATGG

GACCTGCCGATTCCCCATATGCCGGCGGTGTTTTCTTCTTGTCTATCCATTTCCCA

ACCGACTACCCATTCAAGCCACCAAAGATCTCCTTCACAACCAAGATATATCATC

CAAATATCAATGCCAATGGTAACATCTGTCTGGACATCCTAAAGGATCAATGGTC

TCCAGCTCTAACTCTATCGAAGGTCCTATTATCCATCTGTTCTTTGTTAACAGACG

CTAATCCTGACGATCCTTTAGTACCAGAAATCGCTCATATCTACAAGACTGACAG

FIG_3B

ACCCAAGTACGAAGCTACAGCCAGAGAATGGACAAAGAAATACGCTGTAT<u>AAA</u>C
`                                                  TRANSLATION STOP`

AGAAGTCCTTACTCAGCTGAAAAAGAGAAGCAAGATTTATATGGGATTGGACGA

TGAAAAGAATATTAGATACAATGTATTTAAGAAAGAATACAATAAAATATATGTA

TATTCTATCTCTAATAACATAAGATTTACTGATATAAGATATAAGACTATTGTTGGC

AACAGTACAGGGGAACCTTTTTTTTTTTTTCCAAACAACTCGAATCGTAAACCTTA

ATTTAATTTATTCAGGGGAGATTCATGAACATTTTTTTCCTCGAACAGTATGGAGA

ATTTTTGCTTAGTTACATGCACGCAAGCGCGGGTATATCCCGCATATATTTCAGTT

GTGGTTCATATTTGACCTAACTTGTCGAGGGAGCGTCAACGTTAACCGTACCTTTT

TCATTTCTAGTCTATCTGTAGGTTAATTACTATTGTCATTAACATCATTTCTGGGGT

GAAGCCTATTTAAATTTTTGAAGTTCAACGCATAGCTAGTATATGTAATCAACGA

TCAATGACTGGTTCTCTGTTTGGCAAAAATTCTGAGGAGCATTACACTGTACTAA

GGAGGCAGAAGAATAACT<u>GCAG</u>
                   PstI

FIG. 15

AGATCTGCTATTGCATGTGGTGAAAGTTATACCAACATTTTTGCTTATATGAAATC
BglII

ATCTGCAACAACCAATTGGATAAGGATAGATTTCTCAAATATATTAAATTATGTC

TTGGTTTACTTACACAGAAAGTCCCAAAGTACAGATGAATTATACTAGGGTTGTG

TTCATTGTTCCATGAGAGGCTGTACTTTTTGCCTACTTATTTTGGTACTCATTCATT

AGGCTCATAAACCGATTTTTCTTATATTGTGCGTAATTCAATTAGATATCTAGATG

TATTGCTAGTGCTAGTACGGTGTAAACTCTCGTAGCAAGCGTTTTGAAGCATGGC

CATTTGTACCAAAGATAGCCGACCCAAAATTATAAAAAATAATTGTATCCCGGAT

TGTGGTGGAGGTAGTTGCCACTGCGAGCGGGTAATAAAGCGGCTGCCGCCTTACT

TTTAATAGATGGTTGGAGTTTTATTTTCCAAGGTCAGGACTGCTTATTGACTACCA

TCTTGAAAAGTCATTTTCTGCTCACCACCCTCAACTAAACTAAAAATGTCTTCCTC
                                                ORF START

CAAGCGTATTGCCAAGGAATTAAGTGATTTAGGGAGGTATGTTAAAAATAAAAT

AATGATTTTTCTTGATCTGTAAAGAAAAAGGATTACTAACATGAGTTTCTTTTTTG
                                    INTRON
AACTTTTTTCCGAAGAGATCCTCCTGCTTCATGTTCAGCAGGACCTGTAGGGGATG

ACCTGTATCATTGGCAAGCCTCTATTATGGGTCCTTCAGACTCACCCTACGCTGGT

FIG_15A

GGCGTTTTCTTTTTGTCTATTCACTTTCCAACTGATTATCCATTCAAGCCACCGAA

GGTAAACTTTACGACCAAAATTTATCATCCGAATATTAATTCGAGTGGTAATATCT

GCCTTGATATTTTAAAGGACCAGTGGTCACCGGCGCTAACCCTTTCAAAAGTTTTG

TTGTCTATTTGCTCTCTTTTAACAGATGCTAATCCCGACGATCCTTTGGTCCCTGA

AATTGCTCAAATCTACAAGACAGATAAGGCTAAGTATGAAGCCACCGCTAAGGA

GTGGACTAAAAAATATGCTGTTTGATTAATTTGGGCTAACGGATAAATTGTGTAG
| ORF END |

ACTTACCTTCCTCAGCGCACACATCAATATATTATATATTCTTTACGTATACAAAC

ACGCAAATTCTTATAGGTATAGCGATATTAGTTTGATCA
                                    BclI

PROTEIN EXPRESSION STRAINS

FIELD OF THE INVENTION

This invention relates primarily to the development of fungal strains which express proteins at levels substantially higher than the parental strains.

BACKGROUND AND PRIOR ART

For some 20 years, desired foreign proteins have been produced in microorganisms. However, having introduced the necessary coding sequence and obtained expression, much still remains to be done in order to optimise the process for commercial production One area of interest concerns strain improvement, that is to say finding or making strains of the host microorganism which enable the protein to be made in higher yields or better purity, for example.

To increase the yield, once a good expression system (eg transcription promoter) has been devised, one might envisage trying to increase the copy number of the coding sequence (although this will have the desired effect only if DNA transcription was the limiting factor), or to increase the stability of the mnRNA or to decrease the degradation of the protein. Thus, as an example of the latter approach, yeast strains (eg pep4-3) which are deficient in certain proteases have been used for producing desired foreign proteins. In another approach, the number of 2 μm-based plasmids in the yeast Saccharomyces cerevisiae has been increased by introducing a FLP gene into the genome under the control of a regulated promoter, eg GAL. Upon switching to a growth medium containing galactose as the sole carbon source, plasmid copy number rises (11), but the plasmid copy number increase is uncontrolled since the GAL promoter is not repressed by REP1/REP2. This leads to reduced growth rate and thence clonal selection of $cir^o$ derivatives of the original $cir^+$ strain (11,20).

We have mutated yeast strains by application of mutagens in order to generate mutants randomly and thereby hopefully find mutant strains which produce heterologous proteins in better yield (16,21). We have now characterised such a randomly-produced mutant which maintained a higher number of copies of the plasmid expressing the desired protein and have found that the mutation occurred in one of the genes encoding ubiquitin-conjugating enzymes, namely UBC4. The UBC4-encoded enzyme (and the closely related UBC5-encoded) enzyme are involved in degrading aberrant and short lived proteins and there was no reason to have supposed that the deletion of either of them would have enabled an increased yield of a normal, desired, protein to have been obtained.

Several genes encoding ubiquitin conjugating enzymes (UBC) have been implicated in the bulk protein degradation and in the stress response of yeast. UBC1, UBC4 and UBC5 act together to mediate important functions for cell growth and cell viability (2,3). Yeast strains with a mutation in a single gene are viable and have similar growth rates to the parental strains, but ubc4/ubc5 double mutants have reduced growth rates and are sensitive to amino acid analogues, while a triple mutant is inviable, indicating that their activities overlap. The UBC4 and UBC5 genes are closely related and the two coding DNA sequences share 77% identical residues, while the predicted amino acid sequences of the two proteins show 92% identical residues (3). Because of the near identity of the Ubc4 and Ubc5 proteins (hereafter abbreviated to Ubc4p and Ubc5p) it has been suggested that UBC4 could complement for the loss of function of the ubc5 mutant and vice versa (3). This would explain why the dramatic reduction in growth rate was only observed in ubc4/ubc5 double mutants. Pulse chase experiments have indicated that Ubc4p and Ubc5p are responsible for the degradation of short-lived and abnormal proteins, but that the turnover of these proteins was only reduced in strains with the ubc4/ubc5 double mutation. It was not reduced in strains with single ubc4 or ubc5 mutations (3). This reference, therefore, suggested that the use of single ubc4 and ubc5 mutant fungal strains would not be beneficial.

Structurally, all known UBC genes encode a conserved domain (known as the UBC domain) of approximately 16kDa containing the conserved conjugating cysteine (1,22). Transfer of activated ubiquitin results in the covalent attachment of the C-terminus of ubiquitin via a thioester bond to the cysteine residue. UBC genes have been divided into different classes (reviewed in 22). Class I UBC genes are composed almost exclusively of the conserved UBC domain, class II and class III UBC genes have C-terminal or N-terminal extension, respectively, while class IV UBC genes have both C- and N-terminal extensions (22).

The fungal genome is composed of chromosomes, extrachromosomal copies of chromosomal genes, eg nucleosomes, and occasionally stable extrachromosomal elements. These extrachromosomal elements have developed a benignly parasitic relationship with their host, where they successfully balance the theft of cellular resource for the replication and segregation of the element, while not compromising the fitness of the host. General reviews of fligal extrachromosomal elements are covered by references 5 and 6, while the DNA plasmids of the yeasts Saccharomyces species are covered by references 7 and 8 and Kluyveromyces species are covered by reference 9.

The 2 μm plasmids of Saccharomyces species are extrachromosomal DNA species which have evolved mechanisms to ensure their long term autonomous survival without any associated phenotype. The 2 μm plasmid resides in the nucleus and is packaged into chromatin. The plasmid origin of replication acts as an autonomously replicating sequence, while other sequences ensure the maintenance of a controlled high copy number and allow the plasmid to partition uniformly into the daughter cells at mitosis. The plasmid is not required for normal mitotic growth and does not provide the host with any selective advantage since Saccharomyces species devoid of 2 μm plasmid, denoted as $cir^o$, grow only slightly faster than their 2 μm plasmid containing, or $cir^+$, parents.

The 2 μm plasmid is a double stranded circular plasmid of approximately 6,318 bp, comprising two unique regions of 2,774 and 2,346 bp separated by a pair of exact inverted repeats, each 599 bp long (10). In vivo the monomeric plasmid exists as an equal mixture of the two inversion isomers (A and B) that form following site specific recombination between the two inverted repeats. The 2 μm plasmid has four open reading frames known as FLP (also known as A), REP1 (also known as B), REP2 (also known as C) and RAF (also known as D). The plasmid also contains a region, located between RAF and the origin of replication, called STB or REP3, which is composed of a series of imperfect 62 bp repeat elements This element is required in cis, along with the trans acting elements, REP1 and REP2, to enable efficient partitioning of the plasmid between the mother and the daughter cell.

The 2 μm plasmid copy number is also indirectly under the control of chromosomal genes, since it is known that 2 μm plasmid copy number does vary between different Saccharomyces cerevisiae strains and because the chromosomal recessive mutation, known as nib1, results in clonal lethality due to uncontrolled amplification of 2 µm plasmid copy number (39). Yeast strains carrying the nib1 mutation resemble engineered yeast strains where FLP gene expression is galactose induced. The involvement of proteins of the fungal ATP-dependent ubiquitin protein degradation pathway in the regulation of fungal plasmid copy number is not described in the art. Nor is it disclosed that genes of the fungal ATP-dependent ubiquitin protein degradation pathway can be manipulated to control fungal plasmid copy number.

Although the 2 µm plasmid is a very common genetic component of *Saccharomyces cerevisiae*, other yeast strains are known to contain identifiable DNA plasmids, notably the pSR1 and pSB3 plasmids (6,251 bp and 6,615 bp) of *Zygosaccharomyces rouxii*, the pSB1 and pSB2 plasmids (6,550 bp and 5,415 bp) of *Zygosaccharomyces baijii*, the pSM1 plasmid (5,416) of *Zygosaccharomyces fermentati* and the pKD1 plasmid (4,757 bp) of *Kluyveromyces drosophilarum* (9). The most striking feature of all these plasmids is their resemblance to the *Saccharomyces cerevisiae* 2 µm plasmid. Each plasmid is circular, double stranded DNA and is composed of two approximately equally sized halves separated by inverted repeat sequences. Each plasmid contains a single Autonomously Replicating Sequence (ARS) close to one of the inverted repeat sequences and three or four open reading frames, one of which encodes a recombinase which catalyses recombination between the inverted repeats.

A *Saccharomyces cerevisiae* plasmid is considered to be "2 µm-based" if it contains at least one of the 2 µm plasmid elements (ARS, inverted repeat sequences or 2 µm open reading frames), especially the ARS.

SUMMARY OF THE INVENTION

One aspect of the present invention provides a process of producing a fungal cell derived product, comprising (i) providing a fungal cell having a plasmid, the plasmid comprising a functional coding sequence for a protein, and the fungal cell having a modified level of Ubc4p or Ubc5p (hereinafter, generically known as Ubcp activity), and (ii) culturing the cell to produce the fungal cell derived product.

Preferably the fungal cell derived product is a desired protein encoded by the said coding sequence, and the said modified level of Ubcp activity is lower than normal for the cell. This can be tested in vivo by assaying for the rate of abnormal protein turnover (3). The level of Ubcp (Ubc4p and/or Ubc5p) activity may be reduced to at most 50%, 40%, 30%, 20%, 10% or 1% of the wild-type level. Preferably, the cell has a minimal Ubc4p or Ubc5p activity. The cell should not, however, have a low level of both Ubc4p and Ubc5p, since its growth rate will generally be too low to be useful.

The reduction in Ubcp activity can be achieved in any one of a variety of ways. Firstly the cell can produce a compound which interferes with the binding of the UBC-encoded product to its receptor. Hence, a construct may be provided in the cell to express a polypeptide which competes for the binding of Ubc4p or Ubc5p to its target. This will facilitate a reduction in the effective Ubc4p or Ubc5p activity. This may be done by over-expressing the UBC domain encoded by UBC4 or UBC5 described above. It will be important to ensure that the over-expressed UBC domain encoded by UBC4 or UBC5 does not have any intrinsic Ubc4p or Ubc5p activity of its own, since this might actually contribute to the overall Ubc4p or Ubc5p activity. This may be achieved, by site directed mutagenesis, by removing or replacing (for example with an alanine) the cysteine which acts as the acceptor site for the ubiquitin within the UBC domain of UBC4 (or 5) or other conserved amino acids within the UBC domain. Over expression of the inactive UBC domain of UBC4 (or 5) may be achieved from its own endogenous promoter, or from any other convenient promoter. The construct may be integrated into the chromosome or episomal.

Alternatively, in order to achieve a reduced level of Ubcp activity, the endogenous UBC gene may be modified such that substantially no protein is produced therefrom or such that any protein produced therefrom has a reduced level of Ubc4p or Ubc5p activity. Thus, for example, the UBC gene may be deleted (either in a regulatory region or in the coding region or both) such that no polypeptide is produced or a mutant (defective) polypeptide product is produced. (By "regulatory region", we include parts of the genome acting on the UBC gene indirectly, for example a gene producing a UBC gene activator.) Deletion of all or part of the UBC open reading frame (14) is preferred, as this will reduce or abolish Ubcp activity and generate a non-reverting mutant fungal strain. Alternatively, the activity can be reduced or abolished by classical mutagenesis procedures, whereby the DNA sequence of the UBC gene is mutated in such a way as to produce point mutations or deletions which modify and/or disrupt the normal amino acid sequence of the Ubcp. If a mutant Ubcp polypeptide is produced, it may be unstable (ie be subject to increased protein turnover relative to the native protein); or unable to conjugate ubiquitin, or unable to deliver bound ubiquitin to its substrate.

For example, the UBC gene may be modified such that the ubiquitin-accepting cysteine in any protein produced therefrom is absent or of reduced ubiquitin-accepting activity, for example due to alterations in the amino acid residues surrounding or otherwise interacting with the cysteine, as noted above in the context of producing competitive (but inactive) polypeptide. Alternatively, the UBC gene may be modified such that the capacity of any mutant protein produced therefrom is unable to interact with or has reduced affinity for the E1 ubiquitin donor (product of the UBA1 or UBA2 genes). Alternatively, the UBC gene may be modified such that the capacity of any mutant protein produced therefrom to interact with the final ubiquitin acceptor and/or the Ubiquitin ligase (E3) enzyme is absent or reduced. Specifically, mutations (deletion, insertions or substitutions) within the first 21 amino acids of the primary sequence and the first α helix (residues 3–13) of Ubc4p and Ubc5p (29) are preferred as the latter have been implicated in binding of Ubc2p, a related protein, to the ubiquitin protein ligase Ubr1p (33). Especially preferred are mutations affecting the glutamic acid at position 10 (Glu-10) within the primary sequence of Ubc4p and Ubc5p, particularly replacement by lysine (Glu10Lys) or arginine (Glu10Arg).

Alternatively a different promoter may be used to control expression of the UBC gene; such a promoter may be regulatable. For example, it may be inducible, as are promoters of the galactose utilisation pathway, or derepressed by the removal of an inhibitor, as are promoters of the acid phosphatase group.

Site directed mutagenesis or other known techniques can be employed to create single or multiple mutations, such as replacements, insertions, deletions, and transpositions, as described in reference 23. Suitable mutations include chain termination mutations (clearly stop codons introduced near the 3' end might have insufficient effect on the gene product to be of benefit; the person skilled in the art will readily be able to create a mutation in, say, the 5' three quarters of the coding sequence), point mutations that alter the reading frame, small to large deletions of coding sequence, mutations in the promoter or terminator that affect gene expression and mutations that de-stabilize the mRNA. Specific mutations can be introduced by an extension of the gene disruption technique known as gene transplacement (24).

Generally one uses a selectable marker to disrupt a gene sequence, but this need not be the case, particularly if one can detect the disruption event phenotypically. In many instances the insertion of the intervening sequence will be such that a stop codon is present in frame with the UBC sequence and the inserted coding sequence is not translated. Alternatively the inserted sequence may be in a different reading frame to UBC.

A third principal way to achieve a reduction of Ubcp activity is for the cell to produce UBC antisense mRNA. This may be achieved in conventional ways, by including in the cell an expression construct for an appropriate sequence. UBC antisense mRNA may be produced from a constitutive or regulated promoter system (eg promoters of the galactose catabolic pathway), thereby facilitating a reduction in translatable UBC mRNA. Use of the regulated UBC antisense mRNA also allows for control of the ubiquitin-dependent protein degradation pathway by the addition or removal of the activator.

Fungal cells useful in the methods of the invention include the genera Pichia, Saccharomyces, Zygosaccharomyces, Kluyveromyces, Candida, Torulopsis, Hansenula (now reclassified as Pichia), Schizosaccharomyces, Citeromyces, Pachysolen, Debaromyces, Aspergillus, Metschunikowia, Rhodoporidum, Leucosporidum, Botryoascus, Endomycopis, Trichoderma, Cephalosporium, Humicola, Mucor, Neurospora and the like. Preferred genera are Pichia, Saccharomyces, Zygosaccharomyces and Kluyveromyces. Examples of Saccharomyces sp. are *Saccharomyces cerevisiae, Saccharomyces italicus, Saccharomyces diastaticus* and *Zygosaccharomyces rouxii.* Examples of Kluyveromyces sp. are *Kluyveromyces fragilis* and *Kluyveromyces lactis.* Examples of Hansenula sp. are *Hansenula polymorpha* (now *Pichia angusta*), *Hansenula anomala* (now *Pichia anomala*) and *Pichia capsulata.* An example of a Pichia sp. is *Pichia pastoris.* Examples of Aspergillus sp. are *Aspergillus niger* and *Aspergillus nidulans. Yarrowia lipolytica* is an example of a suitable Yarrowiva species.

Preferred are yeast strains, and of these *Saccharomyces cerevisiae* is the particularly preferred host. The yeast strains used can be any haploid or diploid strain of *Saccharomyces cerevisiae,* but in the case of diploid strains it is preferred that the activity of the Ubcp enzyme from both copies of the UBC gene is reduced or abolished.

A number of species have been shown to have homologues of *Saccharomyces cerevisiae* UBC4 and UBC5 genes. UBC4 and UBC5 homologues have been described in *Homo sapiens* (34), *Drosophila melanogaster* (35), *Caenorhabditis elegans* (36), *Arabidopsis thaliana* (37), *Schizosaccharomyces pombe* and *Candida albicans* (38). The *Drosophila melanogaster* and *Caenorhabditis elegans* homologues, UbcD1 and ubc-2, respectively, have also been shown to have Ubcp activity. It can be seen that a homologue need not be termed UBC4 or UBC5; equally, a gene which is called UBC4 or UBC5 need not be a homologue.

Of the known UBC4/UBC5 homologues in the literature, the similarity of the various proteins can be calculated by aligning the primary amino acid sequences. A suitable program is the Megalign Program, Lasergene, DNASTAR Inc, 1228 South Park Street, Madison, Wis. 53715, USA. Using such a program the calculated percentage similarity ranges from 75.7% to 97.3. These values are very high and reflect the highly conserved nature of the Ubc proteins. The highly conserved cysteine residue in the active site occurs at position 193 in the consensus sequence.

Of the other Ubc proteins, the calculated percentage similarity between them and to *Saccharomyces cerevisiae* Ubc4p and Ubc5p ranged from 24.2% to 63.5%. Proteins homologous to the *Saccharomyces cerevisiae* Ubc4p and Ubc5p can therefore be defined as any Class I (as defined by Jentsch, 1992, reference 22) ubiquitin conjugating enzyme, which possesses 66.7% or greater primary amino acid sequence similarity to *Saccharomyces cerevisiae* Ubc4p or Ubc5p, as defined by the Megalign program. A gene is deemed to be homologous to *S. cerevisiae* UBC4 or UBC5 if it encodes such an enzyme.

A number of species have also been shown to possess Ubcp activity. As stated previously ubc4/ubc5 double mutants of *Saccharomyces cerevisiae* have increased doubling time, reduced resistance to amino acid analogues and reduced resistance to heat shock. It is known that the Drosophila UBC1 protein, encoded by the UbcD1 gene, which is 79.6% and 80.3% similar to *Saccharomyces cerevisiae* Ubc4p and Ubc5p respectively, can reverse the phenotypes of a yeast with no Ubc4p or Ubc5p activity when placed downstream of the UBC4 promoter (35). Similarly it is also known that the Caenorhabditis protein ubc-2, encoded by the ubc-2 gene, which is 78.2% and 78.9% similar to *Saccharomyces cerevisiae* Ubc4p and Ubc5p respectively, has the same properties (36). This is therefore a functional test of whether a protein from an unknown source has Ubc4p or Ubc5p activity. It can also be seen that, for the examples of doubling time and survival rate after 24 hrs at 38° C., the single ubc4 or ubc5 mutant strains described by Seufert and Jentsch (3,36) have similar characteristics to the wild-type strain. The Ubcp activity of an unknown Ubc protein, or a mutant form of a known Ubc protein, relative to the natural *Saccharomyces cerevisiae* Ubc4p or Ubc5p, can be determined by its relative ability to return the doubling time or survival rate after 24 hrs at 38° C. (as described in references 3 or 36), of a double ubc4/ubc5 mutant strain to normal for a wild type or single ubc4 or ubc5 mutant *Saccharomyces cerevisiae* strain once the unknown or mutant Ubc protein has been integrated into the *Saccharomyces cerevisiae* genome under the control of the endogenous UBC4 or UBC5 promoter, preferably as a single copy integration at the endogenous UBC4 or UBC5 locus by procedures already described in the literature (36).

In a preferred aspect of the invention, the level of Ubc4p or Ubc5p activity is reduced. This has been found to increase the copy number of an expression plasmid in the cell, and to cause an increased level of expression of a desired protein expressed from the plasmid. Conversely, increasing the level of Ubc4p or Ubc5p activity will reduce the level of expression of the protein, which may be desirable in some circumstances, for, example where the plasmid-encoded protein inhibits production of the desired protein.

The term "desired protein" is used herein in the normal sense to mean any protein (or other polypeptide) which is desired in a given process at a higher level than the one at which the fungal cell would, without human intervention, produce it. The desired protein may be endogenous to the species in question, for example it may be an enzyme which is normally produced by the host cell. Usually, however, the protein is heterologous to the host cell. The protein may perform its required task in the host cell or host cell culture without being extracted. Usually, however, the protein is extracted from the cell culture and purified to some extent for use elsewhere. The protein may be a viral, microbial, fungal, plant or animal protein, for example a mammalian protein. Preferably, it is a human protein, for example albumin, immnunoglobulin or a fragment thereof (such as an Fab fragment or single chain antibody), (haemo-)globin, blood clotting factors (such as factors II, VII, VIII, IX), interferons, interleukins, $\alpha_1$-antitrypsin, insulin, calcitonin, cell surface receptors, fibronectin, pro-urokinase, (pre-pro) chymosin, antigens for vaccines, t-PA, tumour necrosis factor, erythropoietin, G-CSF, GM-CSF growth hormone, plateletderived endothelial cell growth factor, and enzymes generally, such as glucose oxidase and superoxide dismutase. The protein is, of course, not Ubc4p or Ubc5p itself, nor a fusion of either Ubc4p or Ubc5p in which the Ubc4p or Ubc5p performs its natural function.

The desired protein, if it is to be purified from the fungal cell culture, may be obtained by any technique suited to that protein. For example, albumin may be purified from a Saccharoznyces, Kluveromyces or Pichia cell culture according to the techniques disclosed in WO96/37515, EP-625 202 or EP-464 590, respectively.

Our work has principally involved human albumin, although there is no reason to suppose that the process of the invention is applicable only to this protein, especially since the invention has also been shown to be advantageous in the expression of human haemoglobin.

The term "human albumin" is used herein to denote material which is indistinguishable from human serum albumin or which is a variant or fragment thereof. By "variant" we include insertions, deletions and substitutions, either conservative or non-conservative, where such changes do not substantially alter the oncotic, useful ligand-binding or immunogenic properties or albumin. For example we include naturally-occurring polymorphic variants of human albumin or human albumin analogues disclosed in EP-A-322 094. Generally, variants or fragments of human albumin will have at least 50% (preferably at least 80%, 90% or 95%) of human serum albumin's ligand binding activity (for example bilirubin-binding) and at least 50% (preferably at least 80%, 90% or 95%) of human serum albumin's oncotic activity, weight for weight.

The desired protein coding region is preferably contained within a hybrid plasmid comprising a promoter sequence, a DNA coding sequence which is under the transcriptional control of the promoter, a leader sequence directing the secretion of the protein and a DNA sequence containing a eukaryotic transcription termination signal, which plasmid is then maintained as an extrachromosomal DNA sequence or is integrated into one or more chromosomes of the host organism.

Suitable promoters for the expression of the protein include those associated with the phosphoglycerate kinase (PGK1) gene, galactokinase (GAL1) and uridine diphosphoglucose 4-epimerase (GAL10) genes, iso-1-cytochrome c (CYC1), acid phosphatase (PHO5), alcohol dehydrogenase genes (ADH1and ADH2) and MFα-1. The preferred promoters are the glycerol-3-phosphate dehydrogenase (GPD1), described in EP 424 117, and the protease B (PRB1) promoter, described in EP-431 880 B1.

Suitable transcription termination sequences can be the 3' flanking equence of the eukaryotic gene which contains proper signals for transcription termination and polyadenylation in the fungal host, or those of the gene naturally linked to the expression control sequence, or those associated with the phosphoglycerate kinase (PGK1) or the iso-1-cytochrome c (CYC1) gene. The preferred transcription termination sequence is from the alcohol dehydrogenase gene (ADH1).

Suitable secretory leader sequences are, for example, the natural human serum albumin leader sequence, the leader sequence from the *Saccharomyces cerevisiae* MFα-1 leader sequence, the *Kluyveromyces lactis* killer toxin leader, a fusion between the natural human serum albumin leader and the *Saccharomyces cerevisiae* MFα-1 leader sequence, or a fusion between the *Kluyveromyces lactis* killer toxin leader and the *Saccharomyces cerevisiae* MFα-1 leader sequence, or conservatively modified variations of these sequences, as described in WO 90/01063.

Hybrid plasmids may also be used which, apart from the expression control sequence, the heterologous gene sequence and the transcription termination sequence, contain additional sequences which are non-essential or less important for the function of the promoter, ie for the expression of the desired polypeptide, but which perform important functions in, for example, the propagation of the cells transformed with the said hybrid plasmids. The additional DNA sequences may be derived from prokaryotic and/or eukaryotic cells and may include chromosomal and/or extra-chromosomal DNA sequences. For example, the additional DNA sequences may stem from (or consist of) plasmid DNA, such as bacterial, yeast or higher eukaryotic chromosomal DNA. Preferred hybrid plasmids contain additional DNA sequences derived from bacterial plasmids, especially *Escherichia coli* plasmid pBR322 or related plasmids, bacteriophage, yeast 2 μm plasmid, and/or yeast chromosomal DNA.

In the preferred hybrid plasmids for the expression of the heterologous polypeptide, the additional DNA sequences carry a yeast replication origin and a selective genetic marker for yeast. Hybrid plasmids containing a yeast replication origin, eg an autonomously replicating segment (ARS), are extrachromosomally maintained with the yeast cells after transformation and are autonomously replicated upon mitosis. Hybrid plasmids containing sequences homologous to the yeast 2 μm plasmid DNA can be as well. These hybrid plasmids may be integrated by recombination into yeast 2 μm plasmids already present within the cell or may replicate autonomously. The integration vectors of EP-A-251 744 or the "disintegration" vectors of EP-A-286 424 may be used.

Advantageously, the additional DNA sequences which are present in the hybrid plasmids also include a replication origin and a selective marker for the bacterial host, especially *Escherichia coli*, and a selectable marker for the final fungal host. There are useful features which are associated with the presence of an *Escherichia coli* replication origin and an *Esclerichia coli* marker in a yeast hybrid plasmid. Firstly, large amounts of hybrid plasmid DNA can be obtained by growth and amplification in *Escherichia coli* and, secondly, the construction of hybrid plasmids is conveniently done in *Escherichia coli* making use of the whole repertoire of cloning technology based on *Escherichia coli*. *Escherichia coli* plasmids, such as pBR322 and the like, contain both *Escherichia coli* replication original and *Escherichia coli* genetic markers conferring resistance to antibiotics, for example tetracycline and ampicillin, and are advantageously employed as part of the yeast hybrid vectors. The selective fungal marker may be any gene which facilitates the selection of transformants due to the phenotypic expression of the marker. Suitable markers are particularly those expressing antibiotic resistance or, as in the case of auxotrophic yeast mutants, genes which complement host lesions. Corresponding genes confer, for example, resistance to the antibiotic cycloheximide or provide for prototrophy in an auxotrophic yeast mutant, for example the URA1, URA3, LEU2, HIS3, HIS4, TRP5, TRP1 and LYS2 genes.

It has been demonstrated that ftingal cells of the genera Pichia, Saccharomyces, Kluyveromyces, Yarrowia and Hansenula can be transformed by enzymatic digestion of the cell walls to give spheroplasts; the spheroplasts are then mixed with the transforming DNA and incubated in the presence of calcium ions and polyethylene glycol, then transformed spheroplasts are regenerated in regeneration medium. The regeneration medium is prepared in such a way as to allow regeneration and selection of the transformed cells at the same time.

Since the yeast genes coding for enzymes of nucleic acid or amino acid biosynthetic pathways are generally used as selection markers, the regeneration is preferably performed in yeast minimal medium. Methods for the transformation of Saccharomyces cerevisiae are taught generally in EP 251 744, EP 258 067, WO 90/01063 and by Hinnen et al (4), all of which are incorporated herein by reference.

Hence, in its broadest aspect, the invention provides the use of a means to vary UBC4 or UBC5 function in a fungal cell to control the copy number of a plasmid in that cell.

Preferred non-limiting embodiments of the invention will now be described by way of example and with reference to the accompanying drawings, in which:

FIG. 1 is a plasmid map of pDB2277;

FIG. 2 is photograph of a rocket immunoelectrophoresis gel showing the increased rHA productivity of ubc5 disrupted yeast. Strains were as follows: Sample 1, DS569 ura3 [pAYE329/YCplac33]; Samples 2–17, DS569 ura3 [pAYE329/pDB2276] transformants 1–16; Samples 18–33, DS1101 ura3 [pAYE329/pDB2276] transformants 1–16; Samples 34–38 HSA standards 100, 75, 50, 30, and 20 μg/mL HSA;

FIG. 3 is the genomic DNA sequence of the yeast Saccharomyces cerevisiae gene UBC4; the 2.066 kb sequence extends from the PstI site 0.95 kb upstream of the start of the UBC4 open reading frame to the PstI site 0.58 kb downstream of the translation stop codon;

Figure 16:
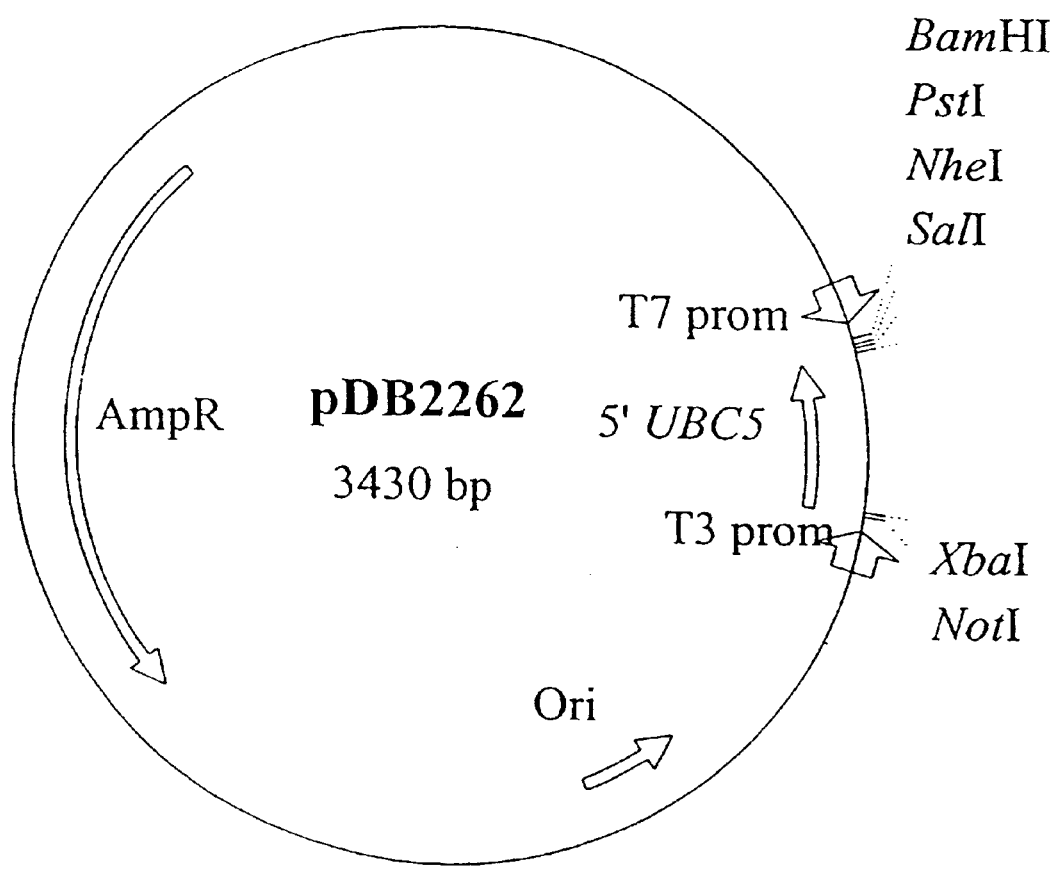
Figure 17:
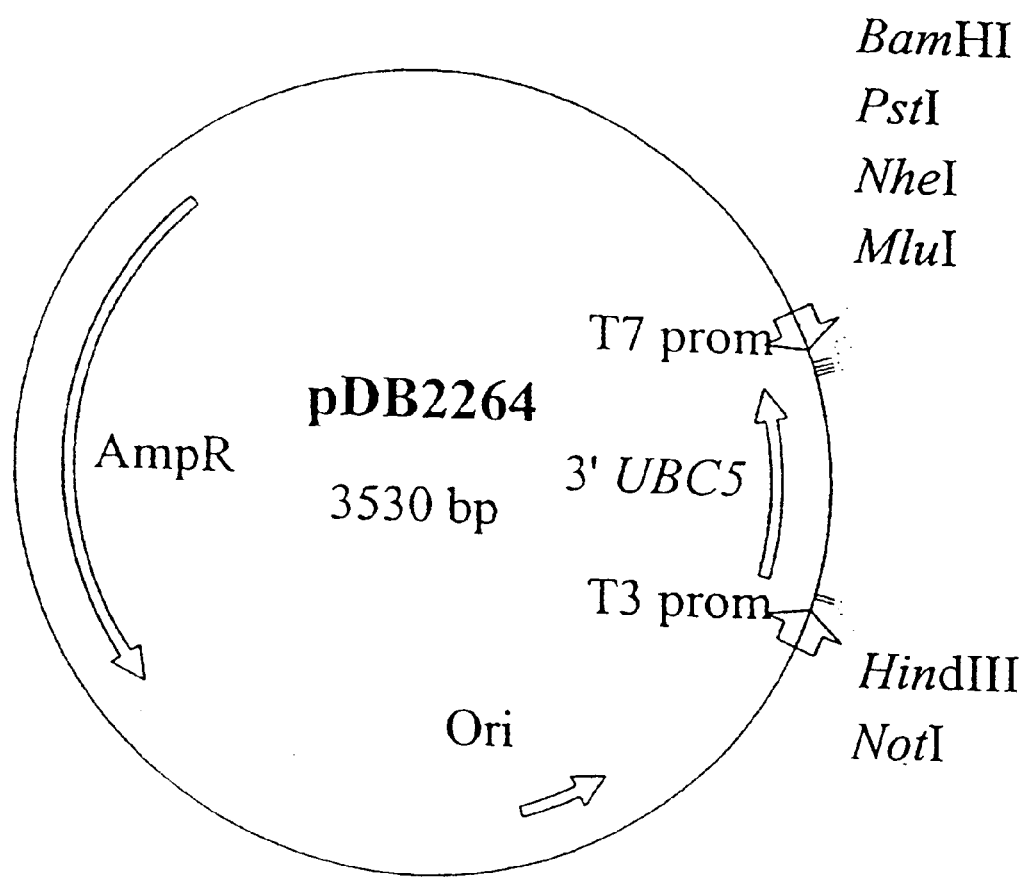
Figure 18:
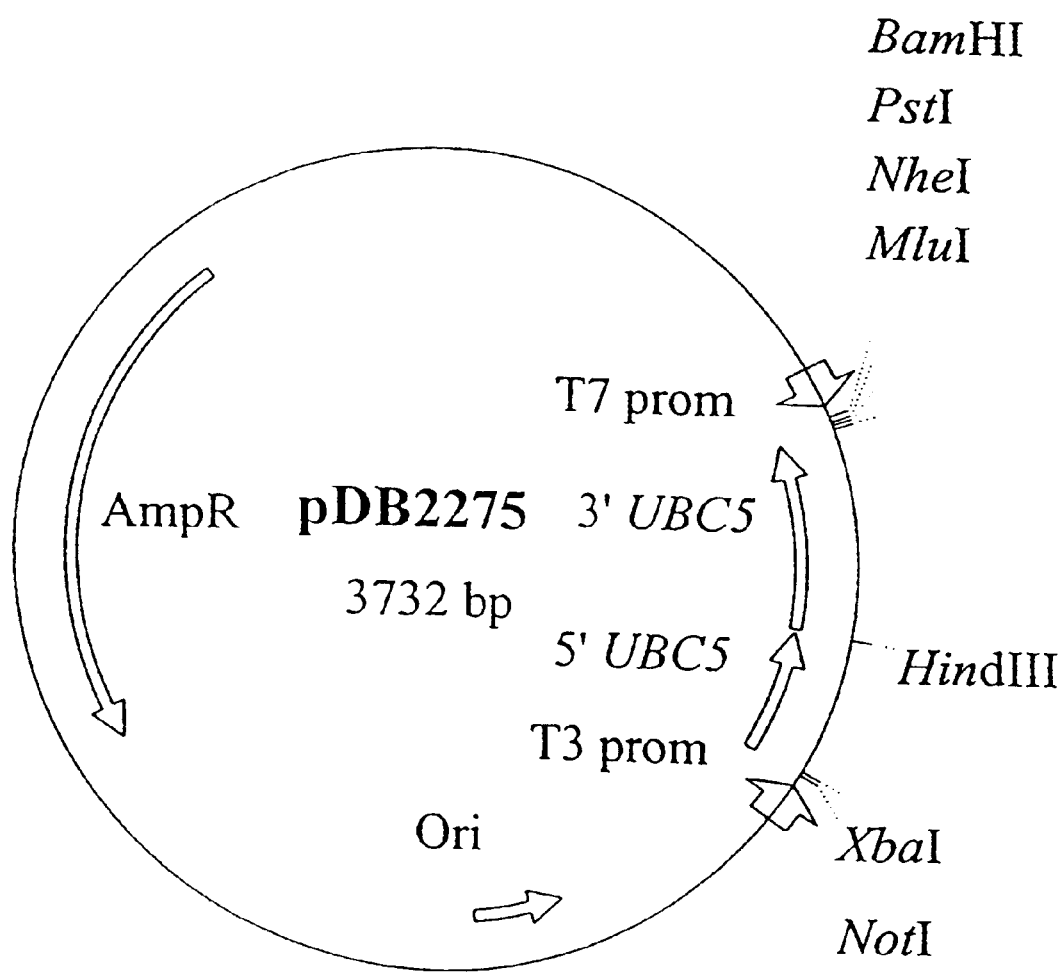

FIG. 15 is the genomic DNA sequence of the Saccharomyces cerevisiae UBC5 gene; the 1.2 kb sequence extends from the BglII site 0.55 kb upstream of the start of the UBC5 open reading frame to the BclI site 0.12 kb downstream of the translation stop codon;

FIG. 16 is a plasmid map of pDB2262;

FIG. 17 is a plasmid map of pDB2264;

FIG. 18 is a plasmid map of pDB2275; and

Figure 19:
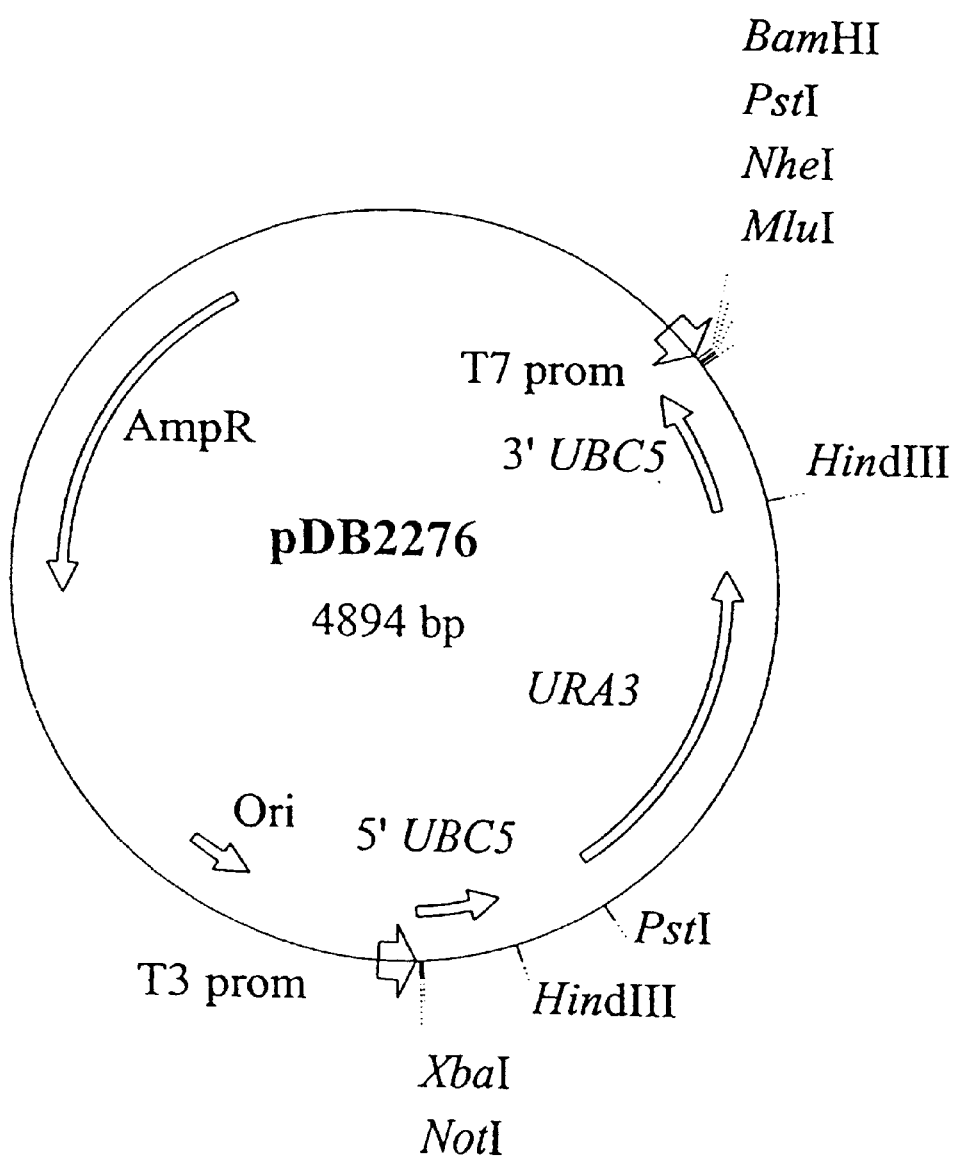

FIG. 19 is a plasmid map of pDB2276.

DETAILED DESCRIPTION OF THE INVENTION

All standard recombinant DNA procedures are as described in reference 13 unless otherwise stated.

EXAMPLE 1

Disruption of the Saccharomyces cerevisiae UBC4 Gene

The Saccharomyces cerevisiae UBC4 gene is located on chromosome II The DNA sequence of the UBC4 gene is shown in FIG. 3.

The UBC4 gene was mutated by the process of gene disruption (14) which deleted the entire UBC4 open reading frame, thereby preventing production of active Ubc4 protein. This was achieved by first amplifying by PCR a suitable marker gene (URA3) with mutagenic single stranded DNA primers which modified the 5' and 3' ends of the URA3 gene so as to include DNA sequences identical to regions 5' and 3' to the UBC4 open reading frame and then transforming a ura3 auxotrophic yeast strain to uracil protoerophy.

Two single stranded oligonucleotide primers (UBC4URA1 and UBC4URA2) suitable for PCR amplification of the 5' and 3' ends of the URA3 gene, incorporating UBC4 sequences at the extremes, were synthesised using an ABI 380B DNA Synthesiser.

```
UBC4URA1   5'TTTCATCGTC CAATCCCATA TAAATCTTGC (SEQ ID NO:1)
           TTCTCTTTTT CAGCTGAGTA AGCTTTTCAA
           TTC ATCTTTT-3'

UBC4URA2   5'-TCTTATTTTT CATCTTAATA AATAATCCAG(SEQ ID NO:2)
           AGAATAAATC TATCCTGAAA AGCTTTTTCT
           TTCCAATTTT-3'
```

PCR reactions were performed to amplify the URA3 gene from the plasmid YEp24 (15). Conditions were as follows: 1 μg/mL plasmid YEp24 DNA, 2 μM of each primer, denature at 94° C. for 30 seconds, anneal to 45° C. for 40 seconds, extend at 72° C. for 120 seconds for 20 cycles, followed by a 72° C. soak for 600 seconds, followed by a 4° C. soak, using a Perkin-Elmer-Cetus Thermal Cycler and a Perkin-Elmer-Cetus PCR kit employing AmpliTaq Thermal Stable DNA Polymerase, total reaction volume 50 μL, according to the manufacturer's instructions. Alternative conditions were, 2 ng/mL plasmid YEp24 DNA, 0.1 μM of each primer, denature at 94° C. for 30 seconds, anneal to 55° C. for 40 seconds, extend at 72° C. for 120 seconds for 30 cycles, followed by a 72° C. soak for 600 seconds, followed by a 4° C. soak, using a Perkin-Elmer-Cetus Thermal Cycler and a Perkin-Elmer-Cetus PCR kit employing AmpliTaq Thermal Stable DNA Polymerase, total reaction volume 50 μL, according to the manufacturer's instructions. The product, 5'-UBC4-URA3-UBC4-3', was analysed by gel electrophoresis and was found to be of the expected size, approximately 1.2 kb. The amplified PCR products were purified using a Promega Wizard PCR DNA purification kit according to the manufacturer's instructions.

The *Saccharomyces cerevisiae* strain DS569 cir⁰ (16) was transformed to leucine prototrophy with the recombinant human albumin (rHA) secretion plasmid pAYE329 (19). The promoter sequence in this plasmid corresponds to that of the *Saccharomyces cerevisiae* NAD-linked glycerol-3-phosphate dehydrogenase (GPD1) gene, rather than the FAD-linked glycerol-3-phosphate dehydrogenase (GUT2) gene as originally described (19).

Figure 4:
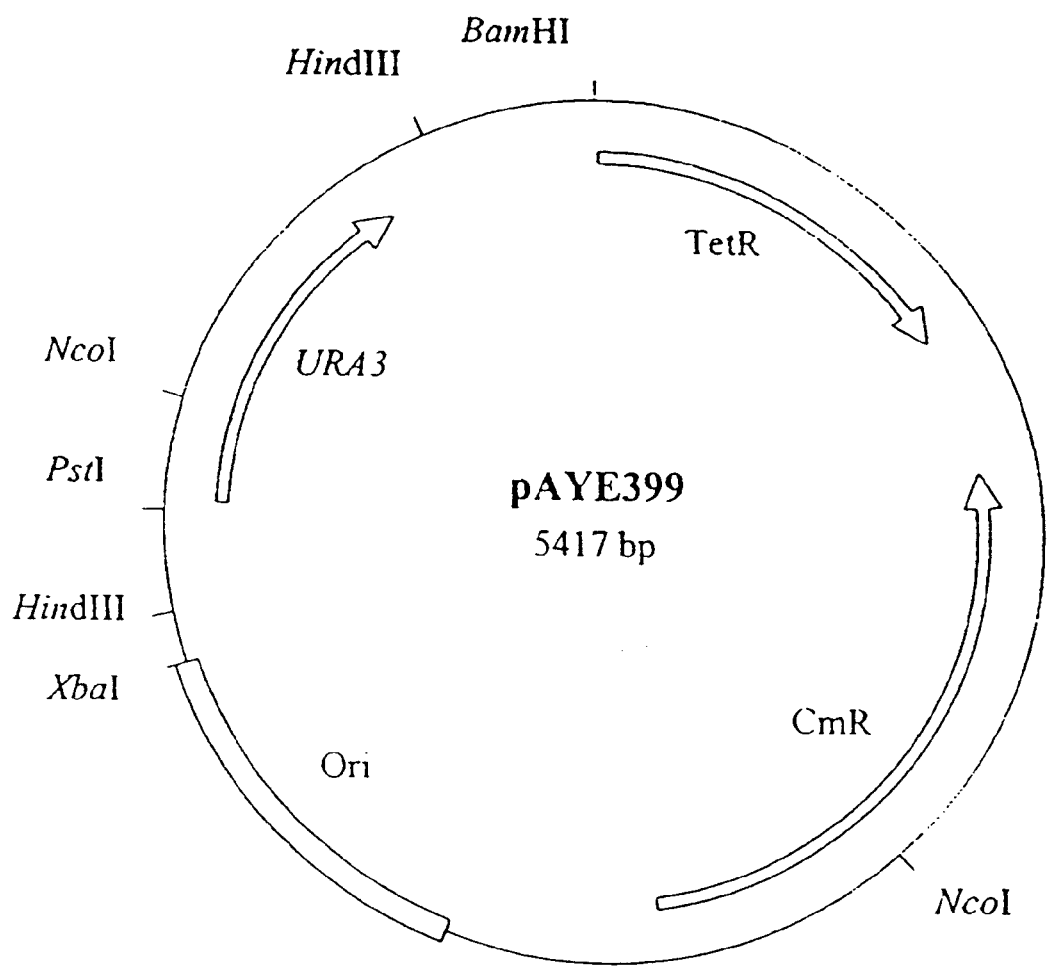
FIG. 4 is a plasmid map of pAYE399.
Figure 5:
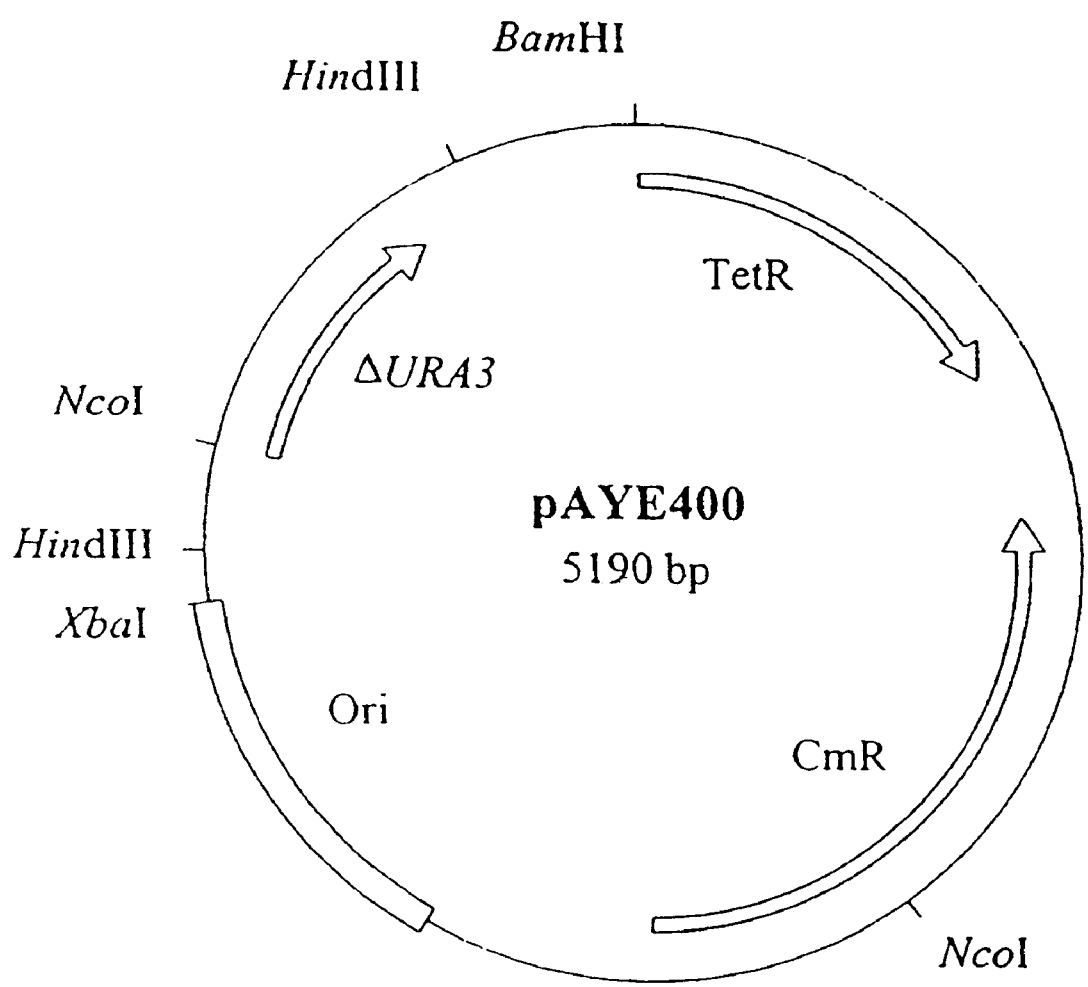
FIG. 5 is a plasmid map of pAYE400.

The ura3 auxotrophic derivative of the *Saccharomyces cerevisiae* strain DS569 [pAYE329] was created by mutating the URA3 gene by the process of gene disruption (14) which deleted part of the URA3 coding sequence, thereby preventing the production of active Ura3 protein. The plasmid YEp24 (15) was digested to completion with HindIII and the products resolved by gel electrophoresis. The 1.17 kb HindIII URA3 gene fragment was isolated and ligated into the unique HindIII site of pACYC184 (17) to create plasmid pAYE399, FIG. 4. Plasmid pAYE339 was digested to completion with PstI and partially digested with NcoI, the products were resolved by gel electrophoresis and the 5.41 kb NcoI-PstI DNA fragment lacking the central part of the URA3 gene was isolated, blunt-end filled with the Klenow fragment of DNA Polymerase and religated. The resultant plasmid pAYE400, FIG. 5, possesses a deletion within the URA3 open reading frame and an NcoI site at the deletion site. The deletion derivative of URA3 gene (ΔURA3) was isolated as a 0.94 kb HindIII fragment from plasmid pAYE400. A ura3 auxotrophic mutant of DS569 [pAYE329] was created by transforming DS569 [pAYE329] with the ΔURA3 0.94 kb HindIII fragment and selecting for Ura⁻ yeast by resistance to 5-fluoro-orotic acid (18). Colonies able to grow on this medium were purified, tested to verify that they were unable to grow in the absence of uracil supplementation and that the defect could be complemented by introduction of the URA3 gene by transformation.

One such strain, DS569 ura3 [pAYE329], was transformed to uracil prototrophy with the 5'-UBC4-URA3-UBC4-3' PCR product. A Southern blot of digested genomic DNA of a number transformants was probed with the UBC4 gene as a 2.07 kb PstI DNA fragment and confirmed the disruption of the UBC4 gene. The new strain was designated UB05 [pAYE329].

These methods are equally applicable to the disruption of UBC4 in any haploid *Saccharomyces cerevisiae* strain. If the desired host already carries a ura3 auxotrophic mutation, then disruption of UBC4 can be performed with the 5'-UBC4-URA3-UBC4-3' PCR product described above. If the desired haploid host does not carry a ura3 auxotrophic mutation, then disruption of UBC4 can be performed once the strain has been made ura3 by transformation with the ΔURA3 0.94 kb HindIII fragment from pAYE400 and selecting for Ura⁻ yeast by resistance to 5-fluoro-orotic acid as described above In the case of a diploid host it is necessary to disrupt both UBC4 genes. This can be achieved by disrupting the UBC4 gene in each of the two parental haploid strains first before diploidisation.

EXAMPLE 2

Disruption of the *Saccharomyces cerevisiae* UBC4 Gene Enhanced the Production of Recombinant Human Albumin The rHA productivity of the yeast strain DS569 [pAYE329] (which does not have a UBC4 disruption) and two independent isolates of UB05 [pAYE329], called UB05-1 [pAYE329] and UB05-6 [pAYE329] (both of which do have a UBC4 disruption) was assessed in 10 mL shake flask culture. Yeast were inoculated into YNB (Difco) minimal medium, buffered with sodium phosphate/citrate pH 6.0 and containing 2% w/v glucose, and incubated at 30° C., 200 rpm for 3 days. The rHA productivity was estimated by rocket immunoelectrophoresis against HSA standards (25–150 µg/mL). The rHA productivity of DS569 [pAYE329] under these conditions was calculated to be 45 mg/L, while the rHA productivity of the two UB05 [pAYE3291 isolates measured under identical conditions was calculated to be 77 and 75 mg/L, respectively.

EXAMPLE 3

Disruption of the *Saccharomyces cerevisiae* UBC4 Gene Increases Hybrid 2 µm Plasmid Copy Number The plasmid copy number of the hybrid 2 µm plasmid of the yeast strains DS569 [pAYE329] and two independent isolates of UB05 [pAYE329], called UB05-1 [pAYE329] and UB05-6 [pAYE329], was assessed in 100 mL shake flask culture. Yeast were inoculated into YNB minimal medium, buffered with sodium phosphate/citrate pH 6.0 and containing 2% w/v glucose, and incubated at 30° C., 200 rpm for sufficient time, usually 1 to 2 days, to allow the culture density to exceed 5 AU/mL, equivalent to mid-logarithmic growth phase. Total genomic DNA was extracted by glass disruption of the yeast cells, followed by solvent extraction, dialysis and ethanol precipitation. The total genomic DNA was digested to completion with HindIII and the products analysed by gel electrophoresis. The ethidium bromide staining of the plasmid specific DNA bands increased relative to the ethidium bromide staining of the ribosomal DNA (rDNA) bands. indicating that the plasmid copy number of the hybrid 2 µm plasmid had increased. Quantitation of the hybrid 2 µm plasmid copy number relative to the copy number of the rDNA was performed by Southern blot analysis with a joint rDNA/HSA cDNA probe. This showed that the plasmid copy number of the hybrid 2 µm plasmid pAYE329 increased from 48.9±9.2 copies per haploid genome in DS569 [pAYE329] to 83.1±12.5 and 116.8±29.0 copies per haploid genome in UB05-1 [pAYE329] and UB05-6 [pAYE329], respectively.

EXAMPLE 4

Antisense UBC4 mRNA Expression.

One way to disrupt expression of the UBC4 gene is to arrange for expression of an antisense polynucleotide.

The antisense transcript can be expressed from a copy, or copies, of the antisense expression cassette which have been integrated into the chromosome(s), or it can be expressed from a low plasmid copy number vector, eg a centromeric vector like YCp50 (25) or YCplac1111, YCplac33, YCplac22 (26) or plasmids p413 through to p416 containing the GAL1, GALL or GALS promoters (27). The antisense transcript can also be expressed from a high plasmid copy number vector like pJDB207 (12), YEp13 or YEp24 (15). All of these expression plasmids or integrating cassettes require a yeast selectable marker eg URA3, HIS3 or TRP1 to facilitate selection during transformation of yeast containing the appropriate auxotrophic marker(s).

The promoter used to drive the expression of the antisense UBC4 or anti-sense UBC5, may be the native promoter, or a related promoter. This has the advantage of promoting expression of the antisense transcript at the same time as the appearance of the sense transcript. In an especially preferred embodiment, the antisense expression cassette is provided on a high plasmid copy number plasmid to ensure an excess of the antisense transcript over the sense transcript Alternative promoters include strong constitutive promoters such as the glycolytic promoters, eg PGK1, PYK1, TDH2/TDH3 and ENO1/ENO2. Use of strong regulated promoters will have the advantage that plasmid copy number can be regulated at the will of the operator. Examples of such promoters are the GAL1, GALL and GALS promoters (Mumberg et al, 27). These galactose-induced promoters have been incorporated into both high and low plasmid copy number vectors, separated from the CYC1 terminator by a multiple cloning site. The example described below utilises a plasmid called p426 GAL1 (Mumberg et al, 27). The antisense UBC4 transcript can be effective in inactivating UBC4 sense transcript only if the host fungal strain contains a proficient UBC4 gene. However, expression of a UBC4 antisense transcript in a ubc4 fungal strain may be beneficial in mopping up other UBC4-like transcripts, so this is an option as well.

Two single stranded oligonucleotide primers (UBC43 and UBC44) suitable for PCR amplification of the UBC4 open reading frame were synthesised using an ABI 380B DNA Synthesiser.

```
UBC43  5'-ATAAACAAGC TTCCAAAAAA ACATGATTTC ACT  (SEQ ID NO.:3)
       GACTATA GAGTACATAC-3'

UBC44  5'-GTAAGGACTT AAGCTTTATA CAGCGTATTT CT   (SEQ ID NO.:4)
       TTGTCCAT TCTCTGGCTG TAGC-3'
```

PCR reactions were performed to amplify the UBC4 gene from genomic DNA prepared from the yeast strain S288C. Conditions were as follows: 5 µg/mL S288C genomic DNA, 2 µM of each primer, denature at 94° C. for 30 seconds, anneal to 45° C. for 40 seconds, extend at 72° C. for 120 seconds for 35 cycles, followed by a 72° C. soak for 600 seconds, followed by a 4° C. soak, using a Perkin-Elmer-Cetus Thermal Cycler and a Perkin-Elmer, Cetus PCR kit employing AmpliTaq Thermal Stable DNA Polymerase, total reaction volume 50 µL, according to the manufacturer's instructions. The product, 5'-(HindIII)-UBC4-(HindIII)-3'; was analysed by gel electrophoresis and was found to be of the expected size, approximately 0.58 kb. The amplified PCR products were purified using a Promega Wizard PCR DNA purification kit according to the manufacturer's instructions. Use of these two primers, UBC43 and UBC44, introduced HindIII sites 5' and 3' to the UBC4 open reading frame.

Figure 6:
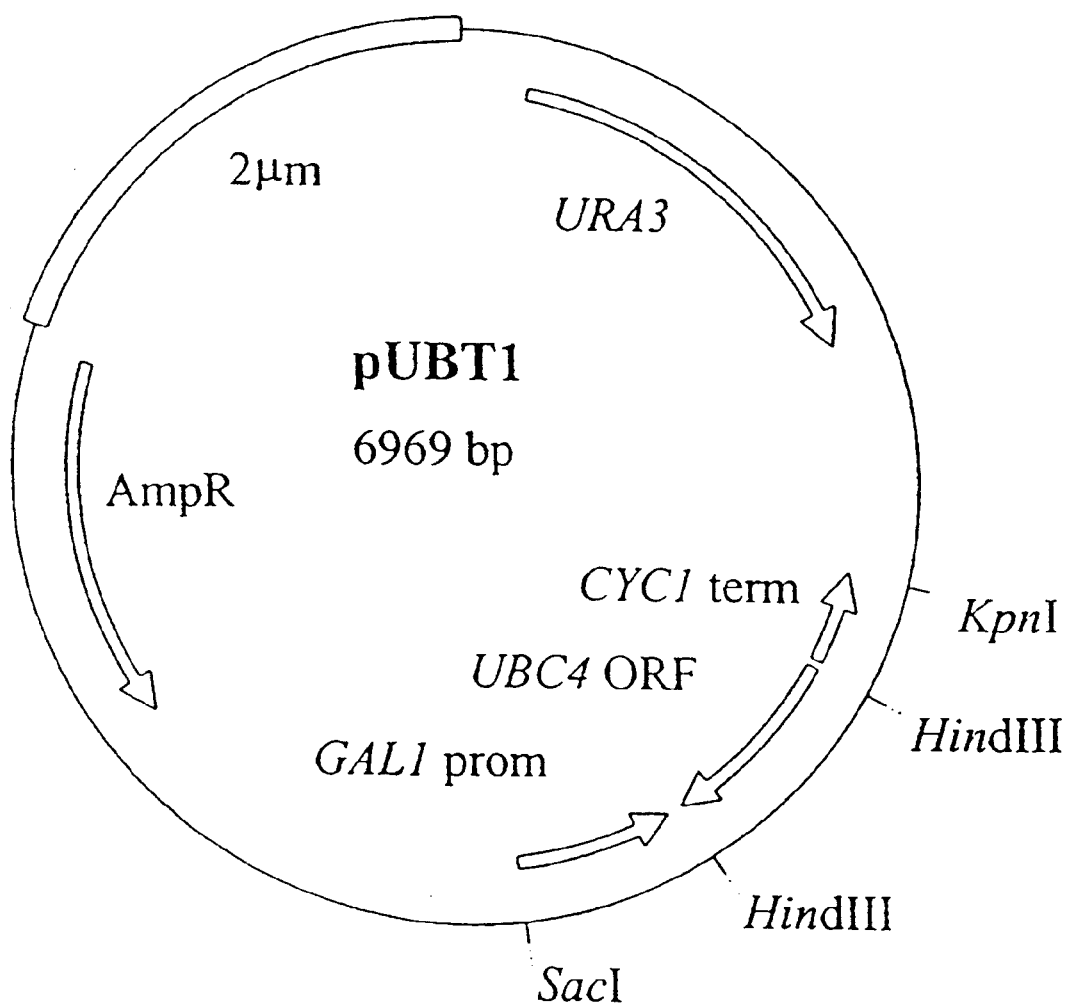
FIG. 6 is a plasmid map of pUBT1.
Figure 7:
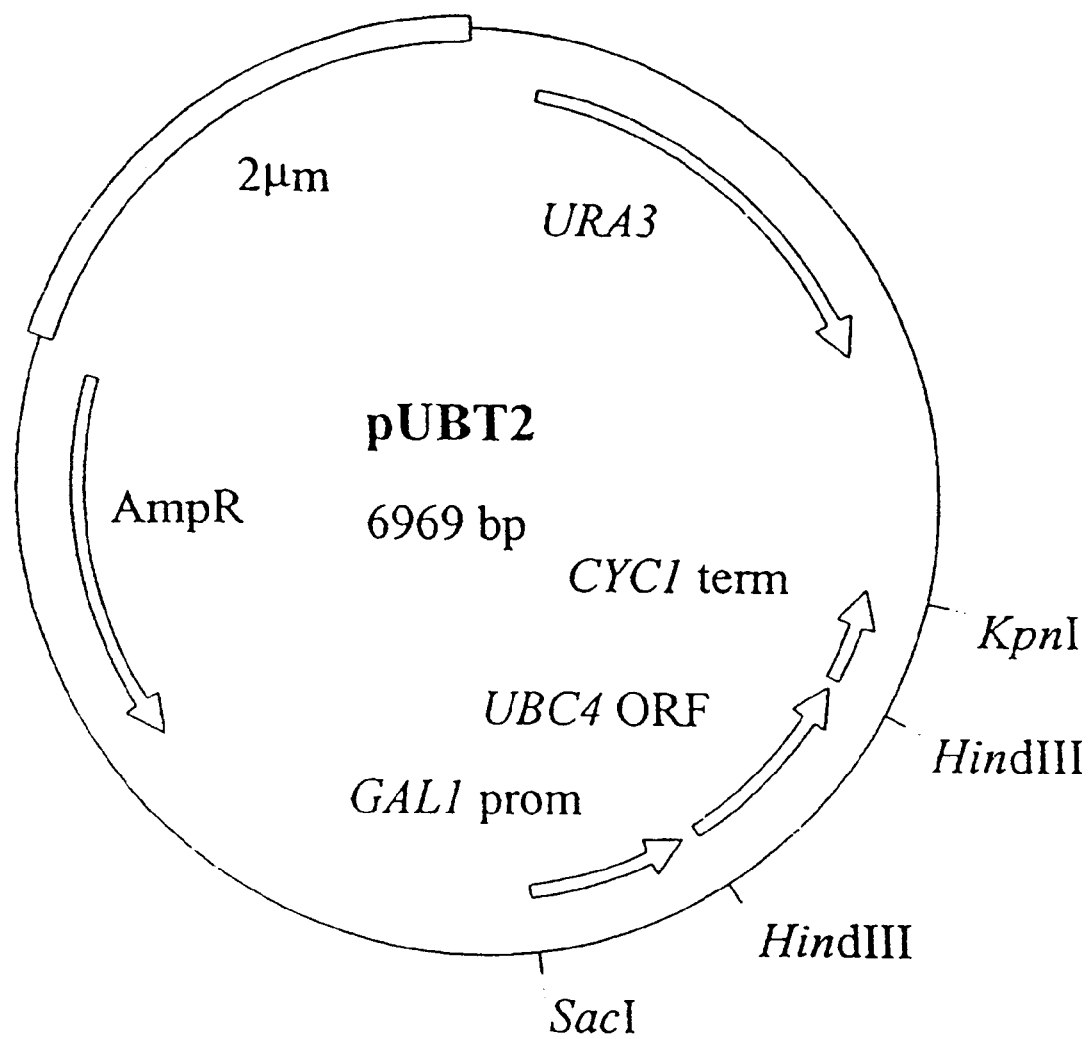
FIG. 7 is a plasmid map of pUBT2.

The purified PCR product, 5'-(HindIII)-UBC4-(HindIII)-3', was digested to completion with HindIII, and ligated into the unique HindIII site situated between the GAL1 promoter and the CYC1 terminator of plasmid p426GAL1 (Mumberg et al, 27) generating two plasmids pUBT1 and pUBT2 (FIGS. 6 and 7). Plasmid pUBT1 contained the UBC4 open reading frame so orientated as to produce an antisense UBC4 transcript from the GAL1 promoter, while plasmid pUBT2 contained the UBC4 open reading frame so orientated as to produce a sense UBC4 transcript from the GAL1 promoter.

Yeast strains deficient in uracil biosynthesis due to the presence of a non-functional ura3 gene, such as DS569 ura3 [pAYE329] (Example 1), were transformed to uracil prototrophy with plasmid pUBT1. UBC4 antisense transcript production was induced by switching from a yeast growth medium containing glucose as the sole carbon source to a medium containing galactose as the sole carbon source. Conversely, UBC4 anti-sense transcript production was repressed by switching from a yeast growth medium containing galactose as the sole carbon source to a medium containing glucose as the sole carbon source.

EXAMPLE 5
Sense UBC4 mRNA Expression from the GAL1 Promoter

Plasmid pUBT2 (FIG. 7) allows for the over-expression of the UBC4 transcript. In a ubc4 deficient fungal strain transformed with plasmid pUBT2, when the carbon source is switched from glucose to galactose, UBC4 mRNA expression will be increased and will force plasmid copy number down. This is yet another way to facilitate control over plasmid copy number by switching between repressing and activating carbon sources. Again this can be done in either a ubc4 or UBC4 background.

Yeast strains deficient in uracil biosynthesis due to the presence of a non-functional ura3 gene, such as DS569 ura3 [pAYE329] (16) or a ura3 derivative of UB05 [pAYE329] (Example 1), were transformed to uracil prototrophy with plasmid pUBT2. UBC4 sense transcript production was induced by switching from a yeast growth medium containing glucose as the sole carbon source to a medium containing galactose as the sole carbon source. Conversely, UBC4 sense transcript production from pUBT2 was repressed by switching from yeast growth medium containing galactose as the sole carbon source to a medium containing glucose as the sole carbon source.

Figure 8:
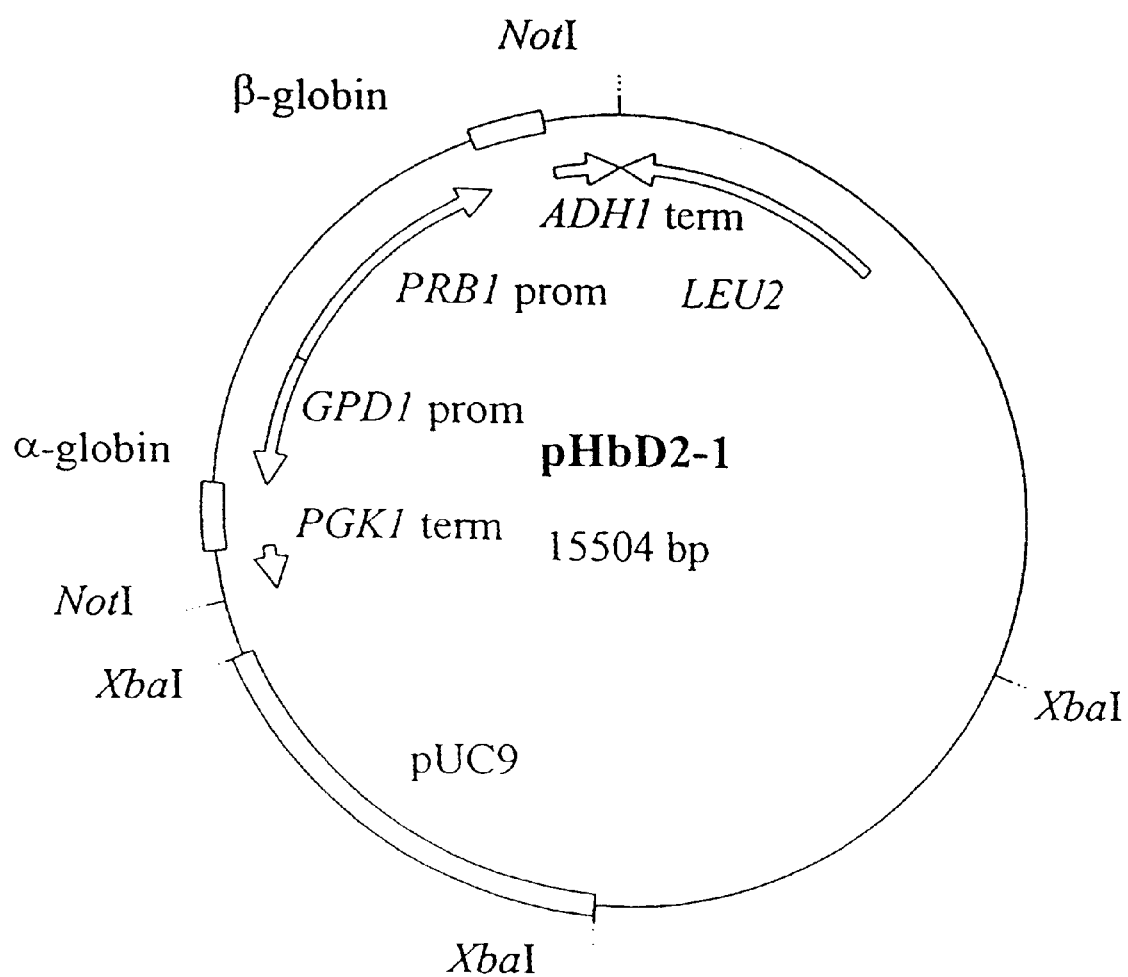
FIG. 8 is a plasmid map of pHbD2-1.

EXAMPLE 6
Disruption of the *Saccharomyces cerevisiae* UBC4 Genes Enhances the Production of other Recombinant Human Proteins Elimination of the ubc4 gene will increase the expression of other heterologous proteins. This was exemplified by analysing the expression level of recombinant human haemoglobin in DS569 and DS1101 (described later in Example 7) which possesses a mutation within the UBC4 open reading frame. The human haemoglobin expression plasmid, called pHbD2-1 (FIG. 8), was based on the whole 2 µm disintegration vector pSAC35 (16). Transcription of the human α-globin chain was directed by the GPD1 promoter (19) and terminated by the PGKI terminator. Transcription of the human β-globin chain was directed from the PRB1 promoter and terminated by the ADH1 terminator (16).

The rHb productivity of the yeast strains DS569 and DS1101 transformed to leucine prototrophy with pHbD2-1 was assessed in 10 mL shake flask culture. Yeast were inoculated into YNB minimal medium, buffered with sodium phosphate/citrate pH 6.0 and containing 2% (w/v) glucose, and incubated at 30° C., 200 rpm for 3 days. The rHb productivity in yeast soluble cell extracts was quantitated by a spectrophotometric assay from the height of the Soret peak in a second derivative spectrum, by comparison with standard HbA of known concentration (28). Total soluble protein concentration was quantitated by Coomassie Protein Assay Reagent, according to the Manufacturer's Instructions (Pierce). The expression level of soluble rHb in DS569 [pHbD2-1] was calculated to be equivalent to 0.4% (w/v) total soluble protein. The expression level of soluble rHb increased to 0.8% (w/v) in the strain DS1101 [pHbD2-1] carrying the ubc4 deletion.

EXAMPLE 7

Mutation of the *Saccharomyces cerevisiae* UBC4 Gene

As described above, the original mutation was produced by random chemical mutagenesis. The starting strain for this process was DS569 [pAYE329] (16). DS569 [pAYE329] was subjected to chemical mutagenesis by N-methyl-N'-nitro-N-nitrosoguanidine (NTG) and potential rHA overexpressing mutant strains selected by a plate screening procedure described in EP431880. One such mutant strain was called DS1101 [pAYE329]. Analysis of the rHA productivity of DS569 [pAYE329] and DS1101 [pAYE329] was performed in 10 mL shake flask culture as described in Example 2. The rHA productivity was estimated by rocket immunoelectrophoresis against HSA standards (25–150 µg/mL). The rHA productivity of DS569 [pAYE329] under these conditions was calculated to be approximately 45 mg/L, while the rHA productivity of DS1101 [pAYE329], measured under identical conditions, was calculated to be 78 mg/L.

The plasmid copy number of the hybrid 2 µm plasmid of the yeast strains DS569 [pAYE329] and DS1101 [pAYE329] was assessed in 100 mL shake flask culture, as described in Example 3. Quantitation of the hybrid 2 µm plasmid copy number relative to the copy number of the rDNA was performed by Southern blot analysis with a joint rDNA/HSA cDNA probe. This showed that the plasmid copy number of the hybrid 2 µm plasmid pAYE329 increased from 48.9±9.2 copies per haploid genome in DS569 [pAYE329] to 70.5±15.9 copies per haploid genome in DS1101 [pAYE329].

To enable the identification of the nature of the original mutation which was responsible for the increased plasmid copy number and rHA productivity observed in DS1101 [pAYE329] a partial Sau3A genomic DNA library was prepared from DS569 high molecular weight genomic DNA in the centromeric vector YCp50 (30). A new yeast strain DS1101 ura3 [pAYE329] was prepared from DS1101 [pAYE329] by the method described in Example 1. DS1101 ura3 [pAYE329] was transformed to uracil prototrophy with DNA from the DS569 YCp50 genomic library. The transformants were assayed for reduced rHA expression by an anti-HSA antibody dependant plate screening procedure described in EP431880. One isolate, DS1101 ura3 [pAYE329/pAYE792], was identified which had reduced rHA productivity when assessed in 10 mL in shake flask culture. Yeast were inoculated into YNB (Difco) minimal medium, buffered with sodium phosphate/citrate pH 6.0 and containing 2% w/v glucose, and incubated at 30° C., 200 rpm for 3 days. The rHA productivity was estimated by rocket immunoelectrophoresis against HSA standards and was shown to be reduced compared to the DS1101 ura3 [pAYE329/YCp50] control, but similar to the DS569 ura3 [pAYE329/YCp50] control. The plasmid copy number of the hybrid 2 µm plasmid of the yeast strains DS569 ura3 [pAYE329/YCp50], DS569 ura3 [pAYE329/pAYE792], DS1101 ura3 (pAYE329/YCp50] and DS1101 ura3 [pAYE329/pAYE792] was assessed in 100 mL shake flask culture, as described in Example 3. Quantitation of the hybrid 2 µm plasmid copy number relative to the copy number of the rDNA was performed by Southern blot analysis with a joint rDNA/HSA cDNA probe. This showed that the plasmid copy number of the hybrid 2 µm plasmid pAYE329 reduced from 59.4±6.0 copies per haploid genome in DS1101 ura3 [pAYE329/YCp50] to 38.3±1.3 copies per haploid genome in DS1101 ura3 [pAYE329/pAYE792], but remained unchanged in DS569 ura3 [pAYE329/YCp50] and in DS569 ura3 [pAYE329/pAYE792] at 33.0±5.3 and 27.5±4.5 copies per haploid genome, respectively.

Figure 9:
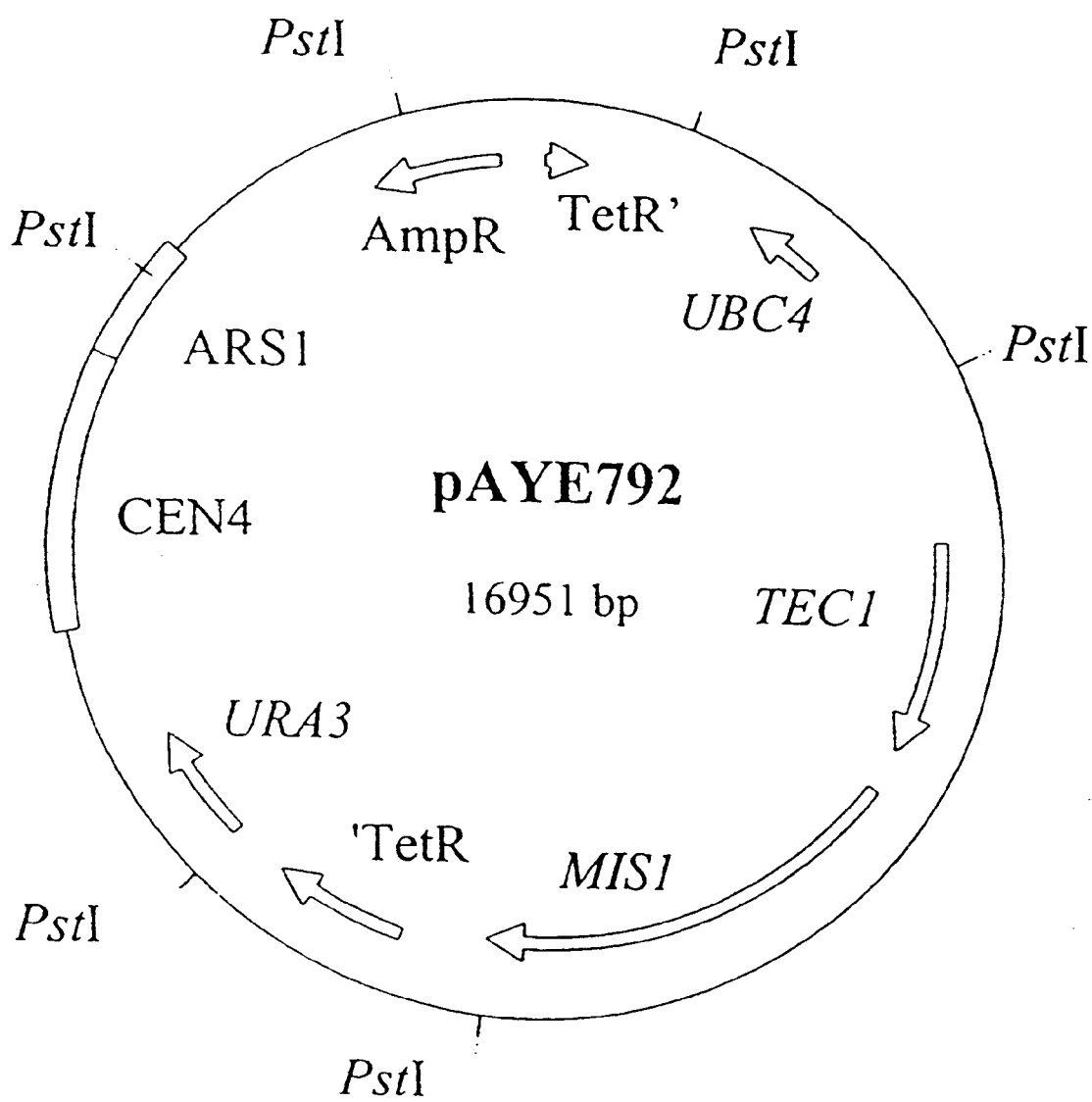
FIG. 9 is a plasmid map of pAYE792.

The pAYE792 centromeric plasmid DNA was isolated from strain DS1101 ura3 [pAYE329/pAYE792] (31) into *E.coli* and DNA sequenced (FIG. 9). This revealed that the plasmid pAYE792 contained a contiguous 9.05 kb genomic insert from chromosome II of *Saccharomyces cerevisiae* (32) spanning the region incorporating the UBC4, TEC1 and MIS1 genes. Subsequent subcloning of the three individual genes showed that the UBC4 gene was responsible for the reduced rHA productivity and reduced plasmid copy number associated with pAYE792 in the strain DS1101 ura3 [pAYE329/pAYE792].

In order to establish the nature of the mutation introduced into DS1101 by the NTG mutagenesis of DS569 the UBC4 gene from DS1101 was isolated by PCR. Two single stranded oligonucleotide primers (UBC4A and UBC4B) suitable for the PCR amplification of the 2.1 kb UBC4 genomic. PstI fragment (FIG. 3) were prepared using an ABI 380B DNA Synthesiser.

```
                                          (SEQ ID NO.: 5)
UBC4A  5'-ACTCCTGCAG TTATTCTTCT GCC-3'

(SEQ ID NO.: 6)
UBC4B  5'-GTGTACAATA AGCTGCAGTA CTC-3'
```

Figure 10:
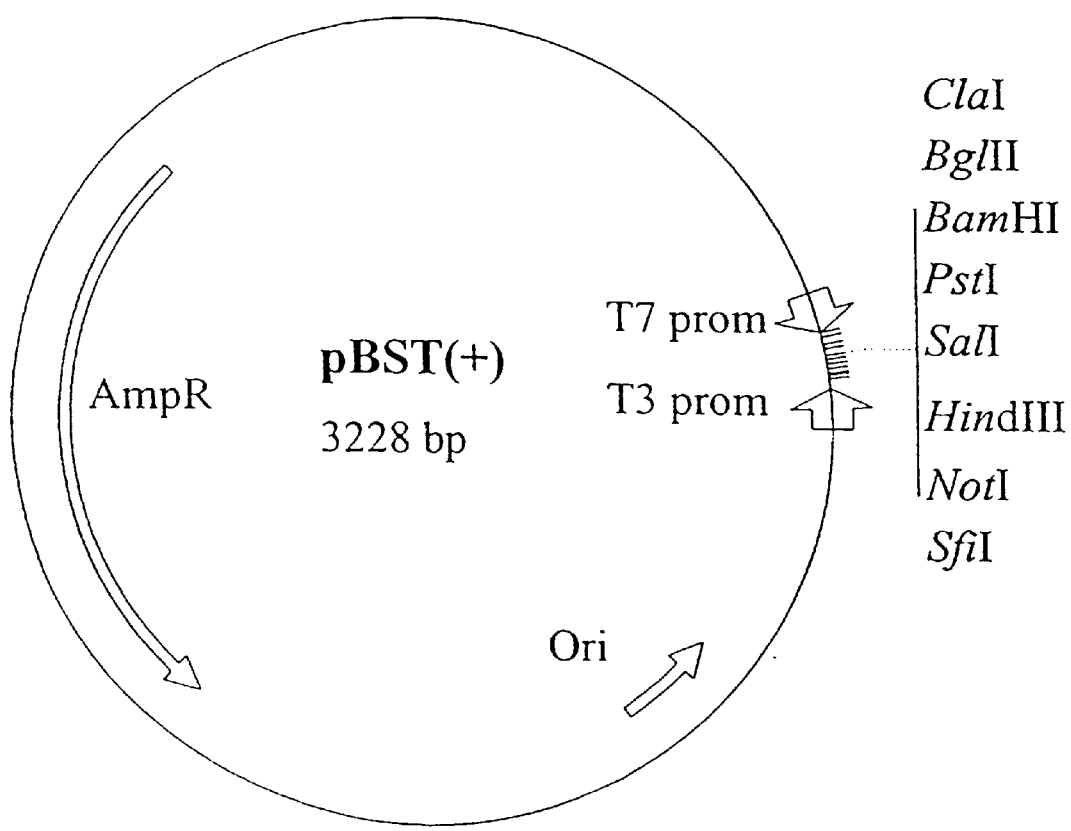
FIG. 10 is a plasmid map of pBST+.
Figure 11:
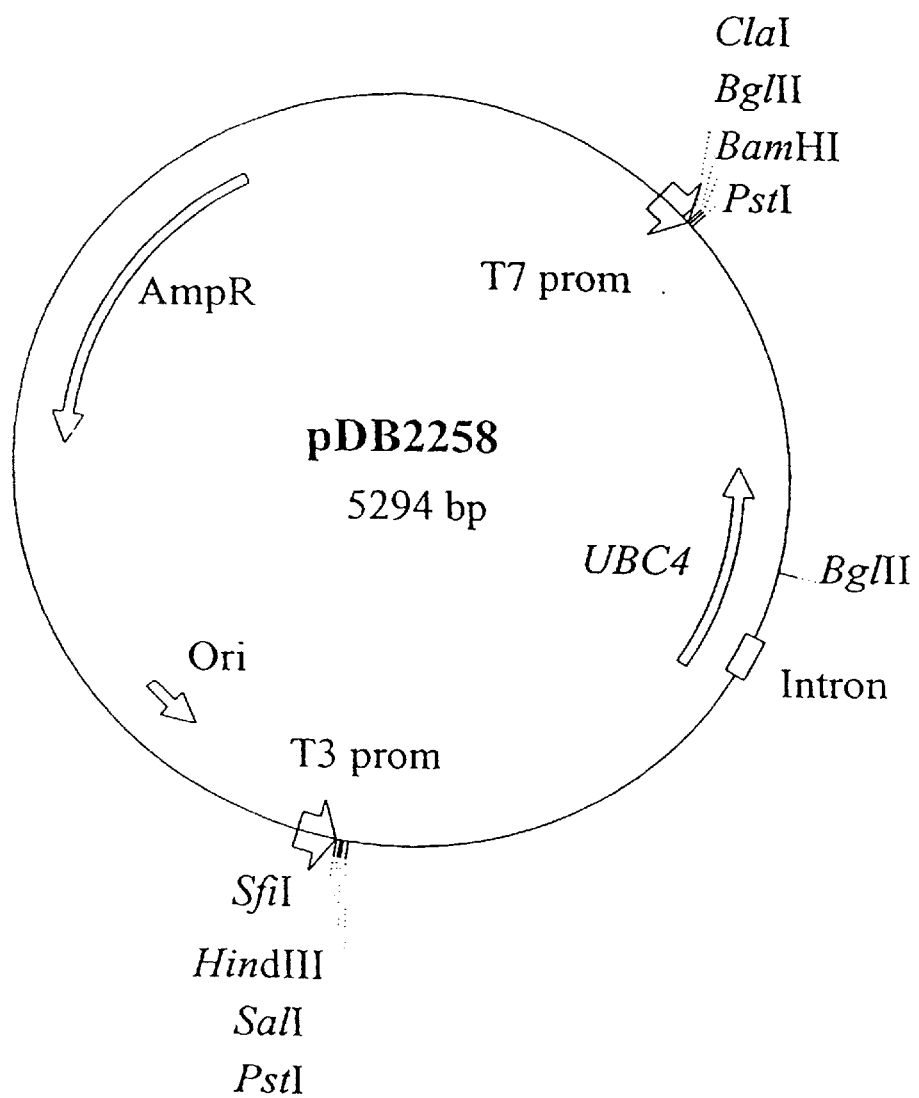
FIG. 11 is a plasmid map of pDB2258.
Figure 12:
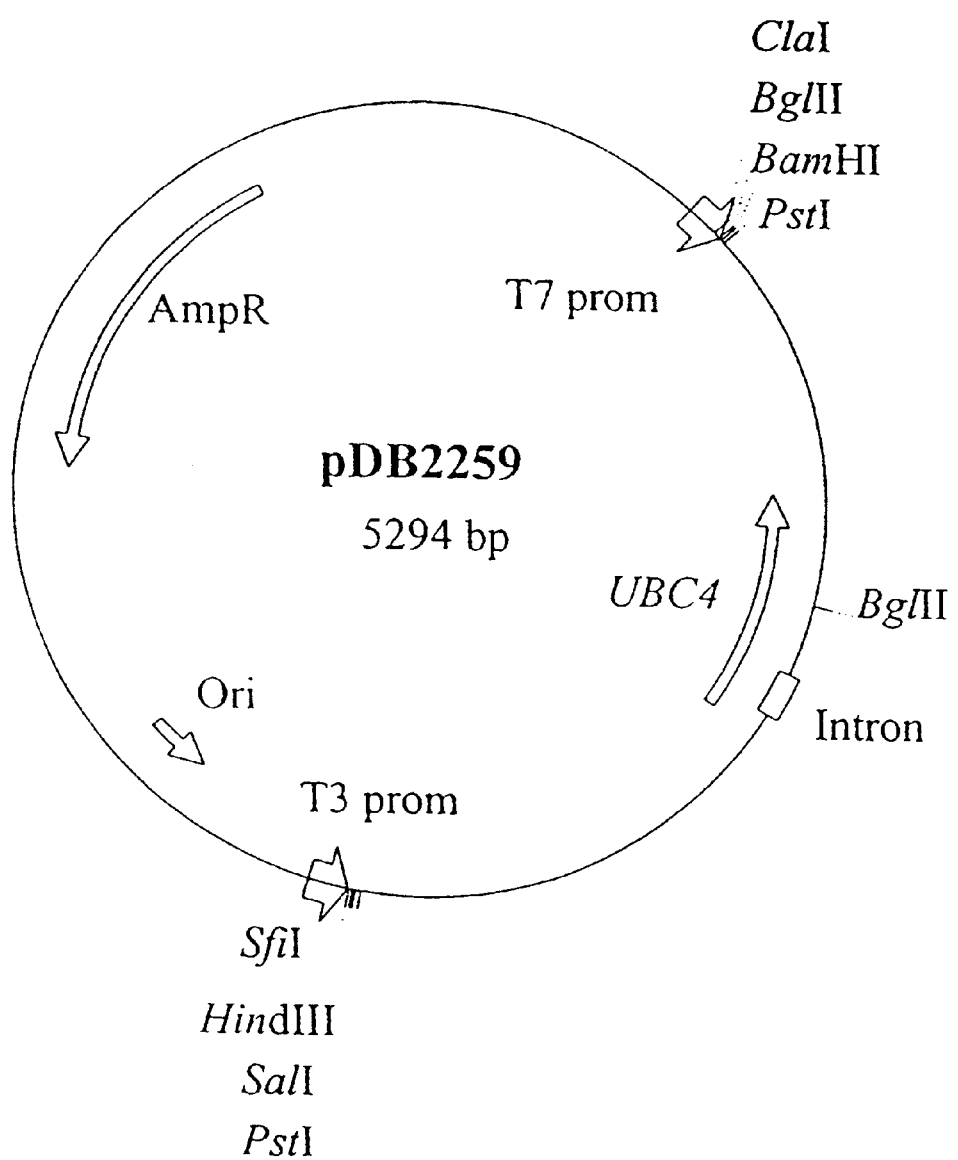
FIG. 12 is a plasmid map of pDB2259.
Figure 13:
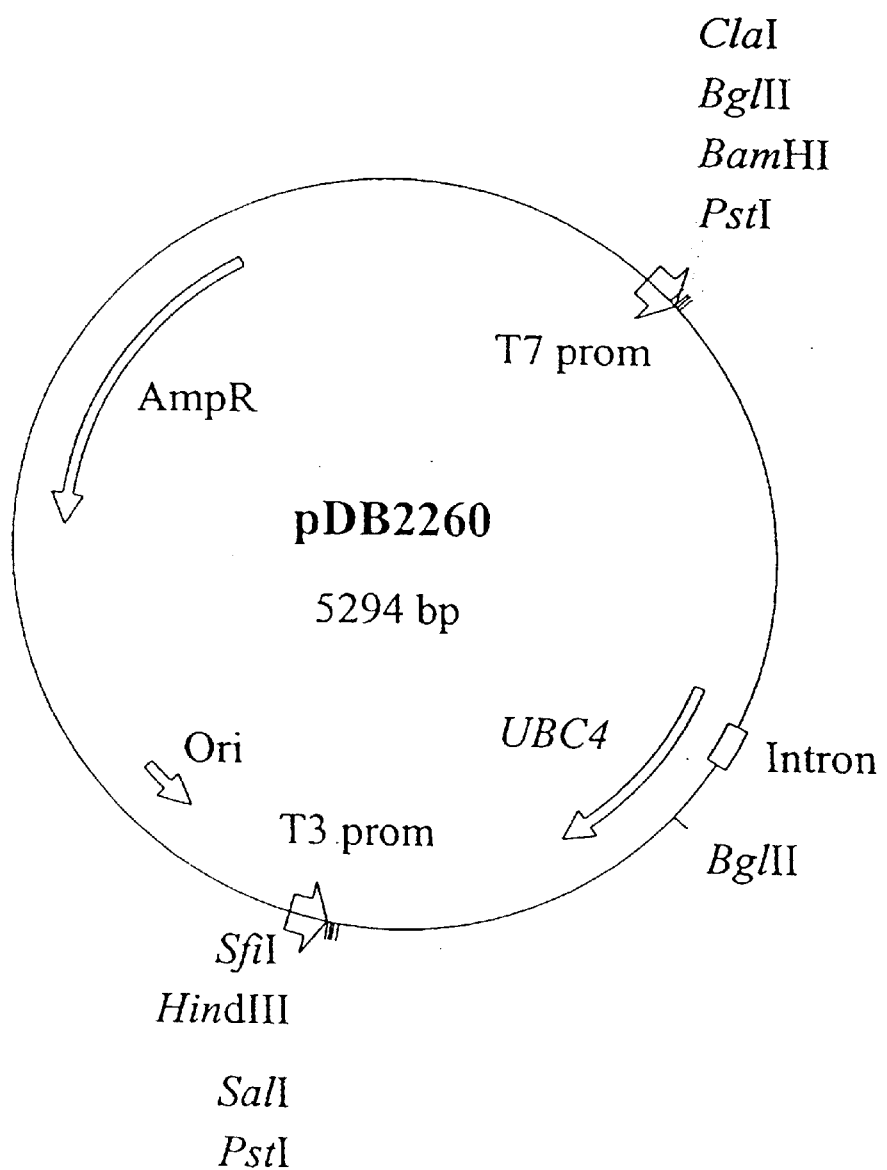
FIG. 13 is a plasmid map of pDB2260.
Figure 14:
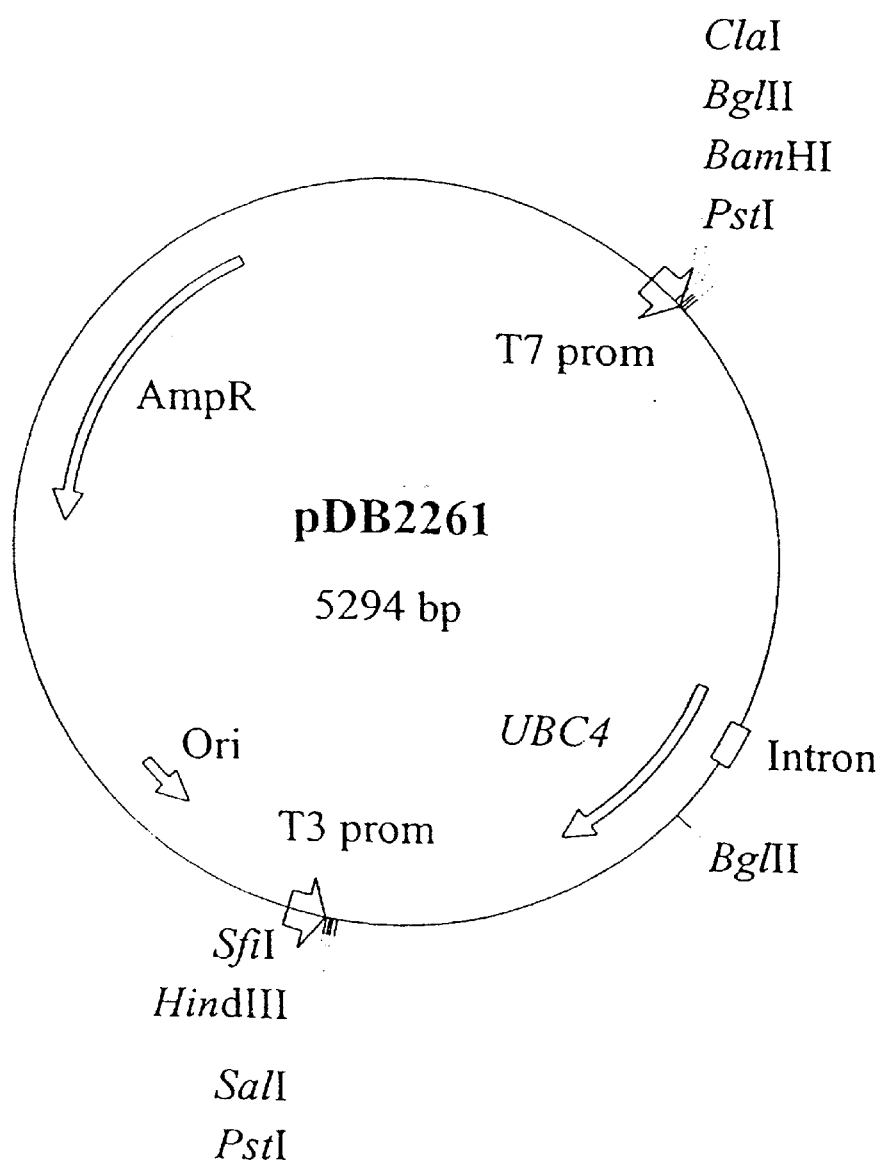
FIG. 14 is a plasmid map of pDB2261.

PCR reactions were performed to amplify the UBC4 gene from high molecular weight genomic DNA prepared from DS1101 according to reference 30. Conditions were as follows: 50 ng/mL to 0.5 ng/nL DS110 genomic DNA, 2 µM of each primer, denature at 94° C. for 30 seconds, anneal to 50° C. for 40 seconds, extend at 72° C. for 120 seconds for 40 cycles, followed by a 72° C. soak for 600 seconds, followed by a 4° C. soak, using a Perkin-Elmer-Cetus Thermal Cycler and a Perkin-Elmer-Cetus PCR kit employing AmpliTaq Thermal Stable DNA Polymerase, total reaction volume 50 µL, according to the manufacturer's instructions. The amplified 2.1 kb DNA product was purified by TAE agarose gel electrophoresis by Geneclean III DNA extraction kit (Bio101 Inc., 1070 Joshua Way, Vista, Calif. 92083, USA) and digested to completion with PstI. The plasmid pBST+ (FIG. 10) was prepared from the phagemid pBS+(Stratagene, 1101 North Torrey Pines Road, La Jolla, Calif. 92037, USA) by digesting pBS+ with EcoRI and HindIII. The isolated linearised vector was ligated with a double stranded oligonucleotide linker with the sequence:

```
5'-
AGCTCCTAGGCCCGGGCGGCCGCAAGCTTGTCGACGCTAGCTGCAGAAGG
 3'-GGATCCGGGCCCGCCGGCGTTCGAACAGCTGCGATCGACGTCTTCC

ATCCAGATCTCGAGGCGCCATCGAT-3'  (SEQ ID NO.:7)
TAGGTCTAGAGCTCCGCGGTAGCTATTAA-5' (SEQ ID NO.:8)
```

Plasmid pBST+ was linearised with PstI and ligated with the PstI digested PCR amplified 2.1 kb UBC4 DNA product to generate four separate plasmid isolates, called pDB2258, pDB2259, pDB2260 and pDB2261 (FIGS. 11–14). The PstI inserts of all four plasmids (DS1101 derived) and the UBC4 gene isolated from pAYE792 (DS569 derived) were DNA sequenced. The DNA sequence analysis revealed a mutation within the DS1101 UBC4 gene. This mutation, a G to an A substitution, was located in the tenth codon and had the DNA sequence:

```
DS569 UBC4 gene:   ATG TCT TCT TCT AAA CGT ATT GCT AAA GAA CTA   (SEQ ID NO.:9)
                   Met Ser Ser Ser Lys Arg Ile Ala Lys Glu Leu   (SEQ ID NO.:10)

DS1101 UBC4 gene:  ATG TCT TCT TCT AAA CGT ATT GCT AAA AAA CTA   (SEQ ID NO.:11)
                   Met Ser Ser Ser Lys Arg Ile Ala Lys Lys Leu   (SEQ ID NO.:12)
```

The mutation was such that it would change the tenth amino acid from a glutamic acid to a lysine, denoted as Glu10Lys.

This mutant form, or indeed any mutant form, of the UBC4 gene can be introduced into any strain in which the UBC4 gene has already been disrupted by URA3, as already described in Example 1, by procedures sunilar to those already described in the literature for the replacement of the endogenous *Saccharomyces cerevisiae* UBC4 gene by the *Caenorhabditis elegans* ubc-2 gene (36). The yeast strain UB05 (Example 1) was transformed to ura3 (Ura–) with the 2.1 kb PstI fragment from either of the plasmids pDB2258, pDB2259, pDB2260 or pDB2261 (FIGS. 11–14) and selecting for Ura⁻ yeast by resistance to 5-fluoro-orotic acid (18). Colonies able to grow on this medium were purified, tested to verify that they were unable to grow in the absence of uracil supplementation and that the defect could be complemented by introduction of the URA3 gene by transformation. Removal of the URA3 gene from the UBC4 locus in UB05 and its replacement by the Glu10Lys mutant form of the UBC4 gene was confirmed by Southern Blot.

EXAMPLE 8
Disruption of the *Saccharomyces cerevisiae* UBC5 Gene

The *Saccharomyces cerevisiae* UBC5 gene is located on chromosome IV. The DNA sequence of the UBC5 gene is shown in FIG. 15.

The UBC5 gene was mutated by the process of gene disruption (14) which deleted the entire UBC5 open reading frame, thereby preventing production of active Ubc5 protein. This was achieved by first amplifying by PCR a suitable marker gene (URA3) with mutagenic single stranded DNA primers which modified the 5' and 3' ends of the URA3 gene so as to include DNA sequences identical to regions 5' and 3' to the UBC5 open reading frame and then transforming a ura3 auxotrophic yeast strain to uracil prototrophy.

Two single stranded oligonucleotide primers (UBC5URA1 and UBC5URA2) suitable for PCR amplification of the 5' and 3' ends of the URA3 gene, incorporatincg UBC5 sequences at the extremes, were synthesised using an ABI 380B DNA Synthesiser.

UBC5URA1 5'-AGGACTGCTT ATTGACTACC ATCT-TGAAAA GTCATTTTCT GCTCACCACC AGCTTTTCAA TTCATCTTTT-3' (SEQ ID NO.:13)
UBC5URA2 5'-TTGATGTGTG CGCTGAGGAA GGTAAGTCTA CACAATTTAT CCGTTAGCCC AGCTTTTTCT TTCCAATTTT-3' (SEQ ID NO.: 14)

PCR reactions were performed to amplify the URA3 gene from the plasimid YEp24 (15). Conditions were as follows: 1 μg/mL plasmid YEp24 DNA, 2 μM of each primer, denature at 94° C. for 30 seconds, anneal to 45° C. for 40 seconds, extend at 72° C. for 120 seconds for 20 cycles, followed by a 72° C. soak for 600 seconds, following by a 4° C. soak, using a Perkin-Elmer-Cetus Thermal Cycler and a Perkin-Elmer-Cetus PCR kit employing AmpliTaq Thermal Stable DNA Polymerase, total reaction volume 50 μL, according to the manufacturer's instructions. Alternative conditions were, 2 ng/mL plasmid YEp24 DNA, 0.1 μM of each primer, denature at 94° C. for 30 seconds, anneal to 55° C. for 40 seconds, extend at 72° C. for 120 seconds for 30 cycles, followed by a 72° C. soak for 600 seconds, followed by a 4° C. soak, using a Perkin-Elmer-Cetus Thermal Cycler and a Perkin-Elmer-Cetus PCR kit employing AmpliTaq Thermal Stable DNA Polymerase, total reaction volume 50 μL, according to the manufacturer's instructions. The product, 5'-UBC5-URA3-UBC5-3', was analysed by gel electrophoresis and was found to be of the expected size, approximately 1.2 kb. The amplified PCR product was purified using a Promega Wizard PCR DNA purification kit according to the manufacturer's instructions.

DS569 ura3 [pAYE329] was transformed to uracil prototrophy with the 5'-UBC5-URA3-UBC5-3' PCR product. A Southern blot of digested genomic DNA of a number of transformants was probed with the UBC5 gene as a 0.5 kb MluI-Asp718 DNA fragment and confirmed the disruption of the UBC5 gene. The new strain was designated UB1 [pAYE329].

In an alternative method to disrupt the UBC5 gene portions corresponding to the 5' and 3' ends of the UBC5 gene were cloned by PCR. Two pairs of single stranded oligonucleotide primers suitable for PCR amplification of the 5' end of the UBC5 gene (DS101 and DS102) and the 3' end of the UBC5 gene (DS103 and DS104), were synthesised using an ABI 380B DNA Synthesiser.

| | | |
|---|---|---|
| DS101 | 5'-TGACGCGGCC GCTCTAGATG TATTGCTAGT GCTAGTACGG TG-3' | (SEQ ID NO.:15) |
| DS102 | 5'-TGACGTCGAC AAGCTTGGAA AATAAAACTC CAACCATC-3' | (SEQ ID NO.:16) |
| DS103 | 5'-TGACAAGCTT GTGTAGACTT ACCTTCCTCA GCGC-3' | (SEQ ID NO.:17) |
| DS104 | 5'TGACGCTAGC ACGCGTCTGA CTTCTAATCA GAAGATTATG GG-3' | (SEQ ID NO.:18) |

PCR reactions were performed to amplify the 5' end of the UBC5 gene. Conditions were as follows: 1000–10 ng/mL S288C genomic DNA, 2 μM DS101 primer, 2 μM DS102 primer, denature at 94° C. for 30 seconds, anneal to 37° C. for 30 seconds, extend at 72° C. for 60 seconds for 30 cycles, followed by a 72° C. soak for 600 seconds, following by a 4° C. soak, using a Perkin-Elmer-Cetus Thermal Cycler and a Perkin-Elmer-Cetus PCR kit employing AmpliTaq Thermal Stable DNA Polymerase, total reaction volume 50 μL, according to the manufacturer's instructions. The product, 5'-UBC5, was analysed by gel electrophoresis and was found to be of the expected size, 229 bp. The amplified PCR product was purified using a Promega Wizard PCR DNA purification kit according to the manufacturer's instructions.

PCR reactions were performed to amplify the 3' end of the UBC5 gene. Conditions were as follows: 1000 . 10 ng/mL S288C genomic DNA, 2 µM DS103 primer, 2 µM DS104 primer, denature at 94° C. for 30 seconds, anneal to 37° C. for 30 seconds, extend at 72° C. for 60 seconds for 30 cycles, followed by a 72° C. soak for 600 seconds, following by a 4° C. soak, using a Perkin-Elmer-Cetus Thermal Cycler and a Perkin-Elmer-Cetus PCR kit employing AmpliTaq Thermal Stable DNA Polymerase, total reaction volume 50 µL, according to the manufacturer's instructions. The product, 3'-UBC5, was analysed by gel electrophoresis and was found to be of the expected size, 327 bp.

Figure 1:
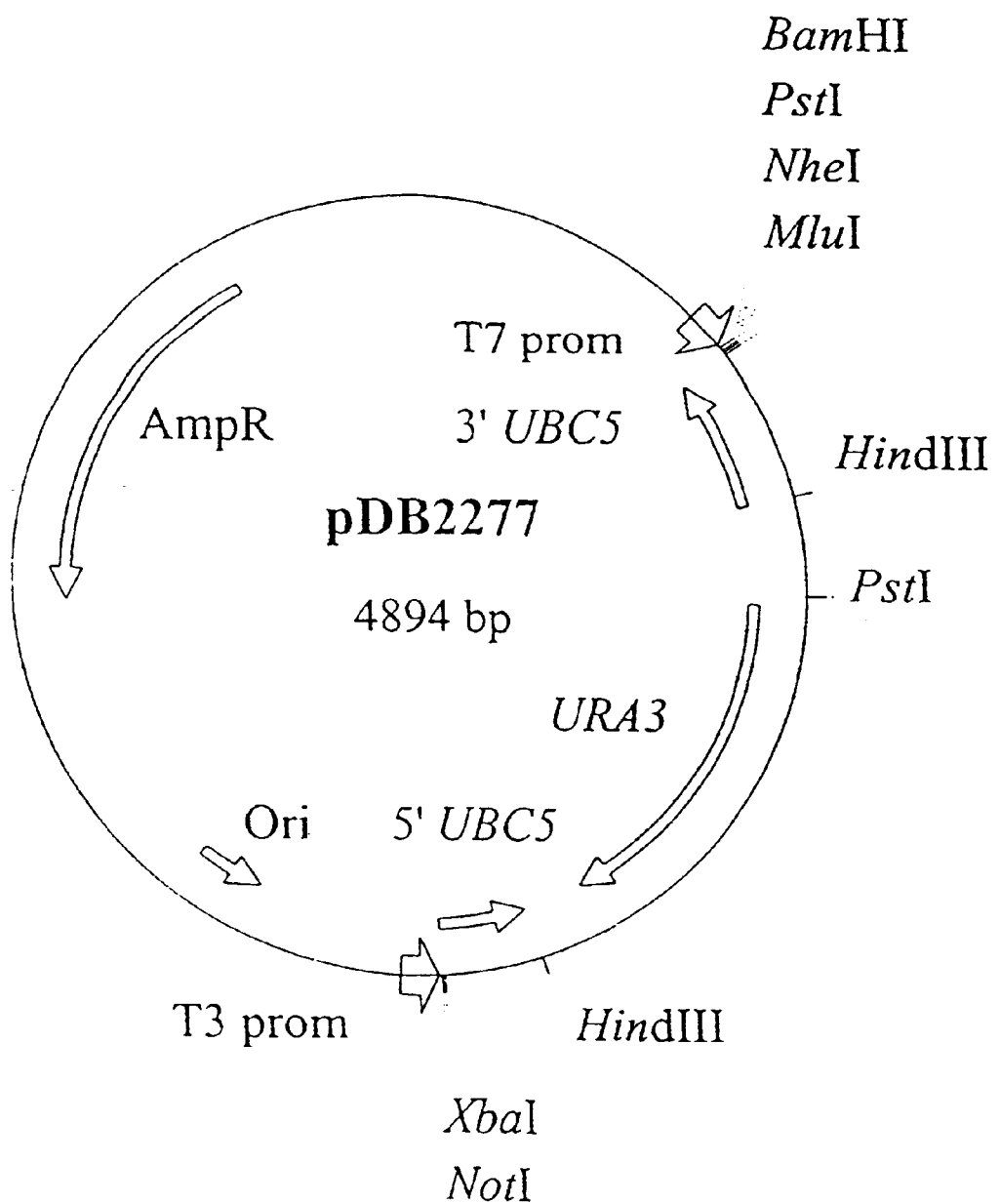

The 5'-UBC5 DNA fragment was digested to completion with NotI and SalI, phenol/chloroform extracted and cloned into NotI/SalI linearised and phosphatased pBST+ to generate plasmid pDB2262 (FIG. 16). The 3'-UBC5 DNA fragment was digested to completion with NheI and HindIII, phenol/chloroform extracted and cloned into NheI/HindIII linearised and phophatased pBST+ to generate plasmid pDB2264 (FIG. 17). The DNA inserts of pDB2262 and pDB2264 were sequenced to confirm their identity. Plasmid pDB2264 was digested to completion with HindIII/NheI and the 327 bp fragment corresponding to the 3' end of UBC5 isolated and cloned into pDB2262, linearised with HindIII/NheI and phophatased. The resultant plasmid called pDB2275 contained the 5' and 3' ends of the UBC5 gene, separated by a unique HindIII site (FIG. 18) The entire genomic URA3 gene isolated as a 1.2 kb HindIII fragment was cloned into linearised pDB2275 with HindIII and phosphatased, generating plasmids pDB2276 (FIG. 19) and pDB2277 (FIG. 1) which only differed from each other by the orientation of the URA3 marker gene.

DS569 ura3 [pAYE329] was transformed to uracil prototrophy with the 5'-UBC5-URA3-UBC5-3' disrupting fragment isolated from either pDB2276 or pDB2277 as 1.7 kb MluI-XbaI fragments. The rHA productivity of these yeast transformants was assessed in 10 mL shake flask culture. Yeast were inoculated into YNB (Difco) minimal medium, buffered with sodium phosphate/citrate pH 6.0 and containing 2% w/v glucose, and incubated at 30° C., 200 rpm for 3 days. The rHA productivity was estimated by rocket immunoelectrophoresis against HSA standards (25–150 µg/mL). The rHA productivity of DS569 [pAYE329] under these conditions was calculated to be approximately 40 mg/L, while the rHA productivity of some of the pDB2276 or pDB2277 transformants measured at the same time was increased to a level greater than that of DS569 [pAYE329], calculated to be approximately 60 mg/L (FIG. 2).

REFERENCES

1. Varshavsky, A. (1992) *Cell* 69, 725–735.
2. McGarth, J. P., et al (1991) *EMBO J.* 10, 227–236.
3. Seufert, W. and Jentsch, S. (1990) *EMBO J.* 9, 543–550.
4. Hinnen, A., et al (1978) *P.N.A.S. (USA)* 75, 1929.
5. Esser, K., et al (1986) "Plasmids of eukaryotes" Springer-Verlag K G, Heidelberg, Germany.
6. Wickner, R. B., et al (1986) "Extrachromosomal elements in lower eukaryotes" Plenum Publishing Corp., New York.
7. Murray, J. A. H. (1987) *Molecular Microbiology* 1, 14.
8. Futcher, A. B. (1988) *Yeast* 4, 2740.
9. Volkert, F. C., et al (1989) *Microbiological Reviews* 53, 299–317.
10. Hartley, J. L. and Donelson, J. E. (1980) *Nature (Lond)* 286, 860–
11. Murray, J. A. H., et al (1987) *EMBO J.* 6, 4205–4212.
12. Beggs, J. D. (1981) "Molecular Genetics in Yeast" Alfred Benz on Symposium 16, 383–395.
13. Maniatis, T., et al (1982) and Sambrook et al (1989) "Molecular Cloning: A Laboratory Manual" Cold Spring Harbor Laboratory, Cold Spring, N.Y.
14. Rothstein, R. J. (1983) *Methods Enzymol.* 101, 203–211.
15. Botstein, D., et at (1979) *Gene* 8, 17–24.
16. Sleep, D., et al (1991) *Bio/Technology* 9, 183–187.
17. Chang, A. C. Y. and Cohen, S. N (1978) *J. Bacteriol.* 134, 1141–1156.
18. Boeke, J. D., et al (1987) *Methods Enzymol.* 154, 164–175.
19. Sleep, D., et at (1991) *Gene* 101, 89–96.
20. Rose, A. B. and Broach, J. R. (1990) *Methods Enzymol.* 185, 234–279.
21. EP-A-0 431 880.
22. Jentsch, D. (1992) *Annu. Rev. Genet.* 26, 179–207.
23. Botstein and Shortle (1985) "Strategies and Applications of In Vitro Mutagenesis" *Science* 229, 193–210.
24. Winston, F. et al (1983) *Methods Enzymol.* 101, 211–228.
25. Rose, M., et al (1987) *Gene* 60, 237–243.
26. Gietz, R. and Sugino, A. (1988) *Gene* 74, 527–534.
27. Mumberg D., et al (1994) *Nuc. Acids Res.* 22, 5767–5768.
28. Ogden, J. E. et al (1994) *Meth. Enz.* 231, 374–390.
29. Cook, W. et al (1993) *Biochemistry* 32, 13809–13817.
30. Rose, M. D. et al (1987) *Gene* 60, 237–243.
31. Lee, F-J, S. (1992) *Biotechniques* 12, 677.
32. Feldmaam, H. et al (1994) *EMBO J.* 13, 5795–5809.
33. Worthylake, et al (1998) *J. Biol. Chem* 273, 6271–6276.
34. Jensen, J. P. et al (1995) *J. Biol. Chem.* 270, 30408–30414.
35. Treier, M. et al (1992) *EMBO. J.* 11, 367–372.
36. Zhen, M. et al (1993) 13, 1371–1377.
37. Girod, P-A. et ac (1993) *Plant J.* 3, 545–552.
38. Damagnez, V. et al (1995) *Gene* 155, 137–138.
39. Holm, C. (1982) *Cell* 29, 585–594.

What is claimed is:

1. A process of increasing the yield of a fungal cell derived product which is heterologous to the cell, comprising
   (i) providing a fungal cell having a plasmid, the plasmid comprising a functional coding sequence for a protein, and the fungal cell having a modified level of Ubc4p or Ubc5p activity, and
   (ii) culturing the cell to produce the fungal cell derived product.

2. A process of increasing the yield of a fungal cell derived product, comprising
   (i) providing a fungal cell having a plasmid, the plasmid comprising a functional coding sequence for a protein, and the fungal cell having a modified level of Ubc4p or Ubc5p activity,
   (ii) culturing the cell to produce the fungal cell derived product, and
   (iii) purifying the fungal cell derived product.

3. A process according to claim 1 or 2 wherein the fungal cell derived product is a desired protein encoded by the said coding sequence, the said modified level of Ubc4p or Ubc5p activity is lower than that of the wild-type fungal cell, and the copy number of the plasmid is increased.

4. A process according to claim 3 wherein the level of Ubc4p or Ubc5p activity is reduced to no more than about 1% of the Ubc4p or Ubc5p activity level of the wild-type fungal cell.

5. A process according to claim 3 wherein the cell produces a compound which interferes with the binding of the Ubc4p or Ubc5p encoded product to its target protein.

6. A process according to claim 3 wherein the UBC gene is modified such that no polypeptide is produced therefrom or any polypeptide produced therefrom is mutated such as to have a reduced level of Ubc4p or Ubc5p activity.

7. A process according to claim 6 wherein at least part of the UBC4 or UBC5 gene is deleted.

8. A process according to claim 6 wherein the UBC4 or UBC5 gene is modified such that the ubiquitin-accepting cysteine in any protein produced from the said gene is absent or of reduced ubiquitin-accepting activity.

9. A process according to claim 6 wherein the UBC4 or UBC5 gene is modified such that any protein produced from the said gene is of reduced ubiquitin-donating activity.

10. A process according to claim 6 wherein the UBC4 or UBC5 gene is modified such that any protein produced from the said gene is of reduced activity as a result of a mutation of one or more of the first 21 amino acids at the N-terminus of the protein.

11. A process according to claim 10 wherein the UBC4 or UBC5 gene is modified such that any protein produced from the said gene is of reduced activity as a result of a mutation in the first α-helix (residues 3–13) of the protein.

12. A process according to claim 10 wherein the UBC4 or UBC5 gene is modified such that any protein produced from the said gene is of reduced activity as a result of a mutation to the glutamic acid at position 10 in the primary sequence.

13. A process according to claim 12 wherein the UBC4 or UBC5 gene is modified such that any protein produced from the said gene is of reduced activity as a result of a lysine or arginine amino acid substitution at position 10 in the primary sequence.

14. A process according to claim 3 wherein the cell produces UBC4 or UBC5 antisense mRNA.

15. A process according to claim 1 or 2 wherein the protein is isolated from the cell culture.

16. A process according to claim 14 wherein the desired protein is a plant protein or animal protein.

17. A process according to claim 16 wherein the desired protein is a human protein.

18. A process according to claim 1 wherein the fungal cell is *Saccharomyces cerevisiae*.

19. A process according to claim 18 wherein the plasmid is a 2 μm-based plasmid.

20. A process for controlling the copy number of a plasmid in a fungal cell comprising the step of varying Ubc4p or Ubc5p activity in said fungal cell.

21. A fungal cell having a reduced level of Ubc4p or Ubc5p activity and having a plasmid, the plasmid having a functional coding sequence for a protein which is albumin, immunoglobulin or a fragment thereof, (haemo-)globin, a blood clotting factor, an interferon, an interleukin, $\alpha_1$-antitrypsin, insulin, calcitonin, a cell surface receptor, fibronectin, pro-urokinase, (pre-pro)-chymosin, an antigen for a vaccine, t-PA, tumour necrosis factor, erythropoietin, G-CSF, GM-CSF, growth hormone, platelet-derived endothelial cell growth factor, glucose oxidase or superoxide dismutase.

22. A fungal cell according to claim 21 wherein the protein is albumin.

23. A fungal cell according to claim 21 wherein the level of Ubc4p or Ubc5p activity is reduced to no more than 50% of the wild-type level.

24. A fungal cell according to claim 22 wherein the level of Ubc4p or Ubc5p activity is reduced to no more than 50% of the wild-type level.

25. A fungal cell according to claim 23 wherein the level of Ubc4p or Ubc5p activity is reduced to no more than about 1% of the Ubc4p or Ubc5-activity level of the wild-type fungal cell.

26. A fungal cell according to claim 24 wherein the level of Ubc4p or Ubc5p activity is reduced to no more than about 1% of the Ubc4p or Ubc5-activity level of the wild-type fungal cell.

27. A fungal cell according to claim 21 wherein the fungal cell is a *Saccharomyces cerevisiae* cell.

28. A fungal cell according to claim 22 wherein the fungal cell is a *Saccharomyces cerevisiae* cell.

29. A fungal cell according to claim 23 wherein the fungal cell is a *Saccharomyces cerevisiae* cell.

30. A fungal cell according to claim 24 wherein the fungal cell is a *Saccharomyces cerevisiae* cell.

31. A fungal cell according to claim 25 wherein the fungal cell is a *Saccharomyces cerevisiae* cell.

32. A fungal cell according to claim 26 wherein the fungal cell is a *Saccharomyces cerevisiae* cell.

33. A fungal cell according to claim 27 wherein the *S. cerevisiae* cell is cir$^\circ$.

34. A fungal cell according to claim 28 wherein the *S. cerevisiae* cell is cir$^\circ$.

35. A fungal cell according to claim 29 wherein the *S. cerevisiae* cell is cir$^\circ$.

36. A fungal cell according to claim 30 wherein the *S. cerevisiae* cell is cir$^\circ$.

37. A fungal cell according to claim 31 wherein the *S. cerevislae* cell is cir$^\circ$.

38. A fungal cell according to claim 32 wherein the *S. cerevisiae* cell is cir$^\circ$.

* * * * *

SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(iii) HYPOTHETICAL: NO (iv) ANTI-SENSE: NO (xi) SEQUENCE DESCRIPTION: SEQ ID NO: 1:

```
TTTCATCGTC CAATCCCATA TAAATCTTGC TTCTCTTTTT CAGCTGAGTA AGCTTTTCAA    60

TTCATCTTTT                                                           70
```

(2) INFORMATION FOR SEQ ID NO: 2:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(iii) HYPOTHETICAL: NO (iv) ANTI-SENSE: NO (xi) SEQUENCE DESCRIPTION: SEQ ID NO: 2:

```
TCTTATTTTT CATCTTAATA AATAATCCAG AGAATAAATC TATCCTGAAA AGCTTTTTCT    60

TTCCAATTTT                                                           70
```

(2) INFORMATION FOR SEQ ID NO: 3:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(iii) HYPOTHETICAL: NO (iv) ANTI-SENSE: NO (xi) SEQUENCE DESCRIPTION: SEQ ID NO: 3:

```
ATAAACAAGC TTCCAAAAAA ACATGATTTC ACTGACTATA GAGTACATAC               50
```

(2) INFORMATION FOR SEQ ID NO: 4:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR PRIMER"

(iii) HYPOTHETICAL: NO (iv) ANTI-SENSE: NO (xi) SEQUENCE DESCRIPTION: SEQ ID NO: 4:

GTAAGGACTT AAGCTTTATA CAGCGTATTT CTTTGTCCAT TCTCTGGCTG TAGC          54

(2) INFORMATION FOR SEQ ID NO: 5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR PRIMER"

(iii) HYPOTHETICAL: NO (iv) ANTI-SENSE: NO (xi) SEQUENCE DESCRIPTION: SEQ ID NO: 5:

ACTCCTGCAG TTATTCTTCT GCC          23

(2) INFORMATION FOR SEQ ID NO: 6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR PRIMER"

(iii) HYPOTHETICAL: NO (iv) ANTI-SENSE: NO (xi) SEQUENCE DESCRIPTION: SEQ ID NO: 6:

GTGTACAATA AGCTGCAGTA CTC          23

(2) INFORMATION FOR SEQ ID NO: 7:

(i) SEQUENCE CHARACTERISTICS:
        (A) LENGTH: 75 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "OLIGONUCLEOTIDE LINKER"

(iii) HYPOTHETICAL: NO (iv) ANTI-SENSE: NO (xi) SEQUENCE DESCRIPTION: SEQ ID NO: 7:

AGCTCCTAGG CCCGGGCGGC CGCAAGCTTG TCGACGCTAG CTGCAGAAGG ATCCAGATCT          60

CGAGGCGCCA TCGAT          75

(2) INFORMATION FOR SEQ ID NO: 8:

(i) SEQUENCE CHARACTERISTICS:
        (A) LENGTH: 75 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "OLIGONUCLEOTIDE LINKER"

(iii) HYPOTHETICAL: NO (iv) ANTI-SENSE: NO (xi) SEQUENCE DESCRIPTION: SEQ ID NO: 8:

AATTATCGAT GGCGCCTCGA GATCTGGATC CTTCTGCAGC TAGCGTCGAC AAGCTTGCGG    60

CCGCCCGGGC CTAGG    75

(2) INFORMATION FOR SEQ ID NO: 9:

(i) SEQUENCE CHARACTERISTICS:
            (A) LENGTH: 33 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 9:

ATGTCTTCTT CTAAACGTAT TGCTAAAGAA CTA    33

(2) INFORMATION FOR SEQ ID NO: 10:

(i) SEQUENCE CHARACTERISTICS:
            (A) LENGTH: 11 amino acids
            (B) TYPE: amino acid
            (C) STRANDEDNESS: <Unknown>
            (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO: 10:

Met Ser Ser Ser Lys Arg Ile Ala Lys Glu Leu
1               5                   10

(2) INFORMATION FOR SEQ ID NO: 11:

(i) SEQUENCE CHARACTERISTICS:
            (A) LENGTH: 33 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 11:

ATGTCTTCTT CTAAACGTAT TGCTAAAAAA CTA    33

(2) INFORMATION FOR SEQ ID NO: 12:

(i) SEQUENCE CHARACTERISTICS:
            (A) LENGTH: 11 amino acids
            (B) TYPE: amino acid
            (C) STRANDEDNESS: <Unknown>
            (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO: 12:

Met Ser Ser Ser Lys Arg Ile Ala Lys Lys Leu
1               5                   10

(2) INFORMATION FOR SEQ ID NO: 13:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR PRIMER"

(iii) HYPOTHETICAL: NO (iv) ANTI-SENSE: NO (xi) SEQUENCE DESCRIPTION: SEQ ID NO: 13:

AGGACTGCTT ATTGACTACC ATCTTGAAAA GTCATTTTCT GCTCACCACC AGCTTTTCAA    60

TTCATCTTTT    70

(2) INFORMATION FOR SEQ ID NO: 14:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR PRIMER"

(iii) HYPOTHETICAL: NO (iv) ANTI-SENSE: NO (xi) SEQUENCE DESCRIPTION: SEQ ID NO: 14:

TTGATGTGTG CGCTGAGGAA GGTAAGTCTA CACAATTTAT CCGTTAGCCC AGCTTTTTCT    60

TTCCAATTTT    70

(2) INFORMATION FOR SEQ ID NO: 15:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR PRIMER"

(iii) HYPOTHETICAL: NO (iv) ANTI-SENSE: NO (xi) SEQUENCE DESCRIPTION: SEQ ID NO: 15:

TGACGCGGCC GCTCTAGATG TATTGCTAGT GCTAGTACGG TG    42

(2) INFORMATION FOR SEQ ID NO: 16:

(i) SEQUENCE CHARACTERISTICS:
        (A) LENGTH: 38 base pairs
        (B) TYPE: nucleic acid (C) STRANDEDNESS: single
        (D) TOPOLOGY: linear (ii) MOLECULE TYPE: other nucleic acid
        (A) DESCRIPTION: /desc = "PCR PRIMER"

(iii) HYPOTHETICAL: NO (iv) ANTI-SENSE: NO (xi) SEQUENCE DESCRIPTION: SEQ ID NO: 16:

TGACGTCGAC AAGCTTGGAA AATAAAACTC CAACCATC        38

(2) INFORMATION FOR SEQ ID NO: 17:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR PRIMER"

(iii) HYPOTHETICAL: NO (iv) ANTI-SENSE: NO (xi) SEQUENCE DESCRIPTION: SEQ ID NO: 17:

TGACAAGCTT GTGTAGACTT ACCTTCCTCA GCGC        34

(2) INFORMATION FOR SEQ ID NO: 18:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR PRIMER"

(iii) HYPOTHETICAL: NO (iv) ANTI-SENSE: NO (xi) SEQUENCE DESCRIPTION: SEQ ID NO: 18:

TGACGCTAGC ACGCGTCTGA CTTCTAATCA GAAGATTATG GG        42

(2) INFORMATION FOR SEQ ID NO: 19:

(i) SEQUENCE CHARACTERISTICS:
        (A) LENGTH: 2072 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 19:

CTGCAGTACT CTTTTGATTC TGTAGGAAAC CAGCGAAGAA CGTACTCTTG CCTGAAGAGA        60

AGTTTTTTTT ATTTATTTAT ATTTTGTTCT GGAAGCTCTT TACAGAATGG AGTAGGAAAA        120

TATATAGAGA GGAAAAGCGA AATCGTTACG AGAATAAATA ATCAAGAAAA GAAACTTGAA        180

CTTGGCTTTT CCAAAACAAC AGAAGTAGCG TTAATTTACT TTCACCGTAA AATTCAACTC        240

```
TTTAAATATA GTCCACTTAG TAAATTCTTG CCAATTTGCA TGATAAATTC GAACCCATTC    300

CTCAAAATAA AGGGTCCTCA TACATTCCAT GGAAAGAAAG TTTTCTTGAA CATTAAGAAT    360

AAAAAGGCAA AAAAGAAAAA AAAAAGCACA GCTACTGTTT TAGTCAACAT TCCTTTCTCA    420

CTGGAATGCA CAAGGTGTCA TTCCTGAACA AGGGTAACTG CACTATTCAT ATGTCCACCT    480

TATGACTTCA TAAAAAGTTT GACAATAAGT AGTCTTACGT GATAAGAAAT GATGTAACAT    540

AAGGCTAATG TCCTTATTCC AAAGTATCTC ATTTATACAA TAAACAAAAC TGATCTTACC    600

GCCTATCCTC CTCTCCGCAC TAATCAATTG TTATAGTTTT TCTCGAAGCG AGGATCAAAT    660

GGCCGAGCAA CAGGAAAAGG AGTACCGGCG GTCACATGGT CTGCGAGATT TTTCCCGCTG    720

CGGAAAAACC TGGCAACAGC TCACCTTGAA AGGCCTTGGC CTGTATTTTT CTTTTTTCTT    780

CATCCTTCTT TCTTTTTCTT TATTCTTATT TTTCATCTTA ATAAATAATC CAGAGAATAA    840

ATCTATCCTG AAAAAAAATA AAGTAAAGAA GCCAGGAAAA TCACTATCGC CACAAGTAAA    900

TAAATTTCAC TGACTATAGA GTACATACAT AAACAAGCAT CCAAAAAAAC ATGTCTTCTT    960

CTAAACGTAT TGCTAAAGAA CTAAGTGATC TAGAAAGGTA TGTCTAAAGT TATGGCCACG   1020

TTTCAAATGC GTGCTTTTTT TTTAAAACTT ATGCTCTTAT TTACTAACAA AATCAACATG   1080

CTATTGAACT AGAGATCCAC CTACTTCATG TTCAGCCGGT CCAGTCGGCG ATGATCTATA   1140

TCACTGGCAA GCATCCATCA TGGGACCTGC CGATTCCCCA TATGCCGGCG GTGTTTTCTT   1200

CTTGTCTATC CATTTCCCAA CCGACTACCC ATTCAAGCCA CCAAAGATCT CCTTCACAAC   1260

CAAGATATAT CATCCAAATA TCAATGCCAA TGGTAACATC TGTCTGGACA TCCTAAAGGA   1320

TCAATGGTCT CCAGCTCTAA CTCTATCGAA GGTCCTATTA TCCATCTGTT CTTTGTTAAC   1380

AGACGCTAAT CCTGACGATC CTTTAGTACC AGAAATCGCT CATATCTACA AGACTGACAG   1440

ACCCAAGTAC GAAGCTACAG CCAGAGAATG GACAAAGAAA TACGCTGTAT AAACAGAAGT   1500

CCTTACTCAG CTGAAAAAGA GAAGCAAGAT TTATATGGGA TTGGACGATG AAAAGAATAT   1560

TAGATACAAT GTATTTAAGA AGAATACAA TAAAATATAT GTATATTCTA TCTCTAATAA   1620

CATAGATTTA CTGATATAAG ATATAAGACT ATTGTTGGCA ACAGTACAGG GGAACCTTTT   1680

TTTTTTTTC CAAACAACTC GAATCGTAAA CCTTAATTTA ATTTATTCAG GGGAGATTCA   1740

TGAACATTTT TTTCCTCGAA CAGTATGGAG AATTTTTGCT TAGTTACATG CACGCAAGCG   1800

CGGGTATACC CGCATATATT TCAGTTGTGG TTCATAATTT GACCTAACTT GTCGAGGGAG   1860

CGTCAACGTT AACCGTACCT TTTTCATTTC TAGTCTATCT GTAGGTTAAT TACTATTGTC   1920

ATTAACATCA TTTCTGGGGT GAAGCCTATT TAAATTTTTG AAGTTCAACG CATAGCTAGT   1980

ATATGTAATC AACGATCAAT GACTGGTTCT CTGTTTGGCA AAAATTCTGA GGAGCATTAC   2040

ACTGTACTAA GGAGGCAGAA GAATAACTGC AG                                 2072
```

(2) INFORMATION FOR SEQ ID NO: 20:

(i) SEQUENCE CHARACTERISTICS:
        (A) LENGTH: 1206 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 20:

-continued

```
AGATCTGCTA TTGCATGTGG TGAAAGTTAT ACCAACATTT TTGCTTATAT GAAATCATCT      60

GCAACAACCA ATTGGATAAG GATAGATTTC TCAAATATAT TAAATTATGT CTTGGTTTAC     120

TTACACAGAA AGTCCCAAAG TACAGATGAA TTATACTAGG GTTGTGTTCA TTGTTCCATG     180

AGAGGCTGTA CTTTTTGCCT ACTTATTTTG GTACTCATTC ATTAGGCTCA TAAACCGATT     240

TTTCTTATAT TGTGCGTAAT TCAATTAGAT ATCTAGATGT ATTGCTAGTG CTAGTACGGT     300

GTAAACTCTC GTAGCAAGCG TTTTGAAGCA TGGCTGTGGT GGAGGTAGTT GCCACTGCGA     360

GCGGGTAATA AAGCGGCTGC CGCCTTACTC ATTTGTACCA AAGATAGCCG ACCCAAAATT     420

ATAAAAAATA ATTGTATCCC GGATTTTAAT AGATGGTTGG AGTTTTATTT TCCAAGGTCA     480

GGACTGCTTA TTGACTACCA TCTTGAAAAG TCATTTTCTG CTCACCACCC TCAACTAAAC     540

TAAAAATGTC TTCCTCCAAG CGTATTGCCA AGGAATTAAG TGATTTAGGG AGGTATGTTA     600

AAAATAAAAT AATGATTTTT CTTGATCTGT AAAGAAAAAG GATTACTAAC ATGAGTTTCT     660

TTTTTGAACT TTTTTCCGAA GAGATCCTCC TGCTTCATGT TCAGCAGGAC CTGTAGGGGA     720

TGACCTGTAT CATTGGCAAG CCTCTATTAT GGGTCCTTCA GACTCACCCT ACGCTGGTGG     780

CGTTTTCTTT TTGTCTATTC ACTTTCCAAC TGATTATCCA TTCAAGCCAC CGAAGGTAAA     840

CTTTACGACC AAAATTTATC ATCCGAATAT TAATTCGAGT GGTAATATCT GCCTTGATAT     900

TTTAAAGGAC CAGTGGTCAC CGGCGCTAAC CCTTTCAAAA GTTTTGTTGT CTATTTGCTC     960

TCTTTTAACA GATGCTAATC CCGACGATCC TTTGGTCCCT GAAATTGCTC AAATCTACAA    1020

GACAGATAAG GCTAAGTATG AAGCCACCGC TAAGGAGTGG ACTAAAAAAT ATGCTGTTTG    1080

ATTAATTTGG GCTAACGGAT AAATTGTGTA GACTTACCTT CCTCAGCGCA CACATCAATA    1140

TATTATATAT TCTTTACGTA TACAAACACG CAAATTCTTA TAGGTATAGC GATATTAGTT    1200

TGATCA                                                               1206
```